US011617505B2

(12) United States Patent
Tsukada et al.

(10) Patent No.: US 11,617,505 B2
(45) Date of Patent: Apr. 4, 2023

(54) OPHTHALMIC SYSTEM, OPHTHALMIC INFORMATION PROCESSING DEVICE, AND OPHTHALMIC DIAGNOSING METHOD

(71) Applicant: TOPCON CORPORATION, Tokyo (JP)

(72) Inventors: Hisashi Tsukada, Hachioji (JP); Yasufumi Fukuma, Wako (JP)

(73) Assignee: TOPCON CORPORATION, Tokyo (JP)

( * ) Notice: Subject to any disclaimer, the term of this patent is extended or adjusted under 35 U.S.C. 154(b) by 463 days.

(21) Appl. No.: 16/633,160

(22) PCT Filed: Feb. 7, 2018

(86) PCT No.: PCT/JP2018/004200
§ 371 (c)(1),
(2) Date: Jan. 23, 2020

(87) PCT Pub. No.: WO2019/021512
PCT Pub. Date: Jan. 31, 2019

(65) Prior Publication Data
US 2021/0153735 A1 May 27, 2021

(30) Foreign Application Priority Data
Jul. 27, 2017 (JP) .............................. JP2017-145634

(51) Int. Cl.
*G06K 9/00* (2022.01)
*A61B 3/00* (2006.01)
(Continued)

(52) U.S. Cl.
CPC .......... *A61B 3/0025* (2013.01); *A61B 3/0058* (2013.01); *A61B 3/102* (2013.01);
(Continued)

(58) Field of Classification Search
None
See application file for complete search history.

(56) References Cited

U.S. PATENT DOCUMENTS

| 2012/0183187 A1 | 7/2012 | Sasaki et al. |
| 2013/0120443 A1 | 5/2013 | Johnsen et al. |

(Continued)

FOREIGN PATENT DOCUMENTS

| JP | 4-052873 A | 2/1992 |
| JP | 2007-195994 A | 8/2007 |

(Continued)

OTHER PUBLICATIONS

Gao ("Automatic Feature Learning to Grade Nuclear Cataracts Based on Deep Learning", IEEE Transactions on Biomedical Engineering, vol. 62, Issue: 11, Nov. 2015, pp. 2693-2701). (Year: 2015).*

(Continued)

*Primary Examiner* — Wei Wen Yang
(74) *Attorney, Agent, or Firm* — Xsensus LLP

(57) ABSTRACT

In an ophthalmic system of some embodiments, ophthalmic imaging apparatuses include slit lamp microscopes, and information processing system is connected to each ophthalmic imaging apparatus via a communication path. Each ophthalmic imaging apparatus is configured to acquire a three dimensional image by photographing a subject's eye, and transmit the three dimensional image to the information processing system. The information processing system is configured to receive the three dimensional image, store three dimensional images received, perform machine learning and/or data mining based on the three dimensional images, store knowledge acquired by the machine learning and/or data mining, and generate diagnosis support information by performing inference based on a three dimensional image of a subject's eye transmitted from one of the (Continued)

slit lamp microscopes knowledge stored in the knowledge storage.

18 Claims, 11 Drawing Sheets

(51) Int. Cl.

| | |
|---|---|
| *G16H 70/60* | (2018.01) |
| *G16H 50/50* | (2018.01) |
| *G16H 30/20* | (2018.01) |
| *G16H 50/70* | (2018.01) |
| *G16H 50/20* | (2018.01) |
| *G16H 30/40* | (2018.01) |
| *G06N 20/00* | (2019.01) |
| *A61B 3/10* | (2006.01) |
| *A61B 3/135* | (2006.01) |
| *A61B 3/14* | (2006.01) |
| *G06T 7/00* | (2017.01) |
| *G16H 40/60* | (2018.01) |

(52) U.S. Cl.
CPC .............. *A61B 3/135* (2013.01); *A61B 3/145* (2013.01); *G06N 20/00* (2019.01); *G06T 7/0012* (2013.01); *G16H 30/20* (2018.01); *G16H 30/40* (2018.01); *G16H 50/20* (2018.01); *G16H 50/50* (2018.01); *G16H 50/70* (2018.01); *G16H 70/60* (2018.01); *G06T 2207/10056* (2013.01); *G06T 2207/20081* (2013.01); *G06T 2207/20221* (2013.01); *G06T 2207/30041* (2013.01); *G16H 40/60* (2018.01)

(56) References Cited

U.S. PATENT DOCUMENTS

| | | | |
|---|---|---|---|
| 2014/0320815 | A1 | 10/2014 | Steinmueller |
| 2015/0085252 | A1* | 3/2015 | Fujimura ............. A61B 3/0025 351/208 |
| 2015/0230773 | A1 | 8/2015 | Cho et al. |
| 2016/0302971 | A1* | 10/2016 | Morley ................. G16H 40/20 |
| 2016/0345822 | A1 | 12/2016 | Fujimura et al. |

FOREIGN PATENT DOCUMENTS

| | | | |
|---|---|---|---|
| JP | 2008-264231 | A | 11/2008 |
| JP | 2012-235796 | A | 12/2012 |
| JP | 2013-248376 | A | 12/2013 |
| JP | 2014-217749 | A | 11/2014 |
| JP | 2015-501667 | A | 1/2015 |
| JP | 2015-154918 | A | 8/2015 |
| JP | 2015-221276 | A | 12/2015 |
| JP | 2016-159073 | A | 9/2016 |
| JP | 2016-179004 | A | 10/2016 |

OTHER PUBLICATIONS

International Search Report and Written Opinion dated May 1, 2018 for PCT/JP2018/004200 filed on Feb. 7, 2018, 10 pages including English Translation of the International Search Report.

* cited by examiner

OPHTHALMIC SYSTEM, OPHTHALMIC INFORMATION PROCESSING DEVICE, AND OPHTHALMIC DIAGNOSING METHOD

CROSS-REFERENCE TO RELATED APPLICATIONS

This application is a national stage (under 35 U.S.C. 371) of International Patent Application No. PCT/JP2018/004200, filed Feb. 7, 2018 claiming priority to Japanese Patent Application No. 2017-145634, filed Jul. 27, 2017, both of which are herein incorporated by reference in their entirety.

FIELD

Embodiments described herein relate generally to an ophthalmic system and an ophthalmic information processing device.

BACKGROUND

Diagnostic imaging serves an important role in the field of ophthalmology. Various kinds of ophthalmic imaging apparatuses are utilized for diagnostic imaging. Examples of an ophthalmic imaging apparatus include a slit lamp microscope, a fundus camera, a scanning laser ophthalmoscope (SLO), an optical coherence tomography (OCT apparatus), and the like. In addition, various kinds of ophthalmic examination apparatuses such as a refractometer, a keratometer, a tonometer, a specular microscope, a wave front analyzer, and a microperimeter are equipped with the function of imaging anterior eye segment and/or the function of imaging eye fundus.

A slit lamp microscope is one of the most widely and frequently utilized apparatuses among various kinds of ophthalmic apparatuses. A slit lamp microscope is an ophthalmic apparatus for illuminating a subject's eye with slit light and observing and/or photographing the illuminated cross section from an oblique position with a microscope. A slit lamp microscope is utilized in general for diagnosis of the anterior eye segment such as the cornea or the crystalline lens. For example, a doctor observes an entire diagnostic site while moving the focal position and the area illuminated by the slit light to determine the presence or absence of abnormality and the extent of abnormality.

Meanwhile, recent advances in artificial intelligence technology have made significant progress in application to various fields. Applications in the medical field cover a wide range, including decision support, data analysis, data mining, transactions (e.g., electronic medical record systems, ordering systems, medical accounting systems, and the like), image processing, image analysis, robots, and genetic analysis.

[PATENT DOCUMENT 1] Japanese Unexamined Patent Application Publication No. 2016-159073
[PATENT DOCUMENT 2] Japanese Unexamined Patent Application Publication No. 2016-179004
[PATENT DOCUMENT 3] Japanese Unexamined Patent Application Publication No. 2007-195994
[PATENT DOCUMENT 4] Japanese Unexamined Patent Application Publication No. 2015-154918
[PATENT DOCUMENT 5] Japanese Unexamined Patent Application Publication No. 2015-501667

As described above, the slit lamp microscope is the most widely and frequently used apparatus in ophthalmology. Therefore, it is considered effective to collect a large number of images acquired with slit lamp microscopes and analyze the collected images using artificial intelligence techniques.

On the other hand, photographing using a slit lamp microscope requires various kinds of operations and manipulations such as moving the illumination system, moving the photographing system, setting the slit width, and setting the focal position. For this reason, doctors often perform photography while operating and manipulating the slit lamp microscope by hand. In addition, it is common to store only a small number of photographed images necessary for diagnosis and informed consent of the subject. Therefore, at present, it is difficult to collect a large number of images acquired by a slit lamp microscope and provide such collected images to artificial intelligence.

An object of the present disclosure is to suitably perform artificial intelligence analysis on images acquired with a slit lamp microscope.

BRIEF SUMMARY

The first aspect of some embodiments is an ophthalmic system that includes a plurality of ophthalmic imaging apparatuses including a plurality of slit lamp microscopes, and an information processing system connected to each of the plurality of ophthalmic imaging apparatuses via a communication path. Each of the plurality of ophthalmic imaging apparatuses includes an image acquisition unit configured to acquire a three dimensional image by photographing a subject's eye, and a first communication unit configured to transmit the three dimensional image to the information processing system. The information processing system includes a second communication unit configured to receive the three dimensional image transmitted by the first communication unit, an image storage configured to store a plurality of three dimensional images received by the second communication unit, a first processor configured to perform at least one of machine learning and data mining, based on the plurality of three dimensional images, a knowledge storage configured to store knowledge acquired by the first processor, and a second processor configured to generate diagnosis support information by performing inference based on a three dimensional image of a subject's eye transmitted from one of the plurality of slit lamp microscopes and received by the second communication unit and based on the knowledge stored in the knowledge storage.

The second aspect of some embodiments is the ophthalmic system of the first aspect, wherein the second processor includes an interested region identifier configured to identify an interested region of the three dimensional image of the subject's eye by analyzing the three dimensional image.

The third aspect of some embodiments is the ophthalmic system of the second aspect, wherein the second processor is configured to generate diagnosis support information by performing inference based on the interested region and the knowledge stored in the knowledge storage.

The fourth aspect of some embodiments is the ophthalmic system of any of the first to third aspects, wherein the plurality of ophthalmic imaging apparatuses includes one or more of modality apparatuses of one or more types different from a slit lamp microscope, the ophthalmic system further includes a fusion image constructing unit configured to construct a fusion image by composing a three dimensional image acquired by one of the plurality of slit lamp microscopes and an image acquired by one of the one or more modality apparatuses, and the second processor is configured to generate diagnosis support information by performing inference based on the fusion image and the knowledge stored in the knowledge storage.

The fifth aspect of some embodiments is the ophthalmic system of the fourth aspect, wherein the one or more modality apparatuses include one or more optical coherence tomography (OCT) apparatuses, and the fusion image constructing unit is configured to construct a fusion image by composing a three dimensional image acquired by one of the plurality of slit lamp microscopes and an image acquired by one of the one or more OCT apparatuses.

The sixth aspect of some embodiments is the ophthalmic system of any of the first to fifth aspects, wherein the image acquisition unit is configured to further acquire a front image by photographing the subject's eye, the first communication unit is configured to transmit the front image together with the three dimensional image, the second communication unit is configured to receive the three dimensional image and the front image transmitted by the first communication unit, the image storage is configured to store a plurality of three dimensional images and a plurality of front images received by the second communication unit, the first processor is configured to perform at least one of machine learning and data mining, based on the plurality of three dimensional images and the plurality of front images, the knowledge storage is configured to store knowledge, based on the plurality of three dimensional images and the plurality of front images, acquired by the first processor, and the second processor is configured to generate diagnosis support information by performing inference based on a three dimensional image and a front image of a subject's eye transmitted from one of the plurality of slit lamp microscopes and received by the second communication unit and based on the knowledge stored in the knowledge storage.

The seventh aspect of some embodiments is The ophthalmic system of any of the first to sixth aspects, wherein each of the plurality of ophthalmic imaging apparatuses further includes a receiving unit configured to receive subject information, the first communication unit is configured to transmit the subject information together with the three dimensional image, the second communication unit is configured to receive the three dimensional image and the subject information transmitted by the first communication unit, the image storage is configured to store a plurality of three dimensional images and a plurality of pieces of subject information received by the second communication unit, the first processor is configured to perform at least one of machine learning and data mining, based on the plurality of three dimensional images and the plurality of pieces of subject information, the knowledge storage is configured to store knowledge, based on the plurality of three dimensional images and the plurality of pieces of subject information, acquired by the first processor, and the second processor is configured to generate diagnosis support information by performing inference based on a three dimensional image of the subject's eye and subject information transmitted from one of the plurality of slit lamp microscopes and received by the second communication unit and based on the knowledge stored in the knowledge storage.

The eighth aspect of some embodiments is an ophthalmic information processing device that includes a communication unit configured to receive three dimensional images of subject's eyes acquired by a plurality of ophthalmic imaging apparatuses via a communication path, the plurality of ophthalmic imaging apparatuses including a plurality of slit lamp microscopes, an image storage configured to store a plurality of three dimensional images received by the communication unit, a first processor configured to perform at least one of machine learning and data mining, based on the plurality of three dimensional images, a knowledge storage configured to store knowledge acquired by the first processor; and a second processor configured to generate diagnosis support information by performing inference based on a three dimensional image of a subject's eye transmitted from one of the plurality of slit lamp microscopes and received by the communication unit and based on the knowledge stored in the knowledge storage.

The ninth aspect of some embodiments is an ophthalmic information processing device that includes a knowledge storage configured to store knowledge acquired by performing at least one of machine learning and data mining based on a plurality of three dimensional images acquired by a plurality of ophthalmic imaging apparatuses including a plurality of slit lamp microscopes, a communication unit configured to receive a three dimensional image of a subject's eye acquired by a slit lamp microscope via a communication path, and a processor configured to generate diagnosis support information by performing inference based on the three dimensional image and the knowledge stored in the knowledge storage.

The tenth aspect of some embodiments is an ophthalmic diagnosing method that includes: photographing subject's eyes and acquiring a plurality of three dimensional images by a plurality of ophthalmic imaging apparatuses; transmitting the plurality of three dimensional images to an information processing system via a communication path; receiving the plurality of three dimensional images by the information processing system; storing the plurality of three dimensional images by the information processing system; acquiring knowledge by performing at least one of machine learning and data mining based on the plurality of three dimensional images by the information processing system; storing the knowledge by the information processing system; and generating diagnosis support information by performing inference based on a three dimensional image of a subject's eye transmitted from a slit lamp microscope and the knowledge stored in the knowledge storage.

Some embodiments are capable of suitably performing artificial intelligence analysis on images acquired by a slit lamp microscope.

DETAILED DESCRIPTION

Figure 1:
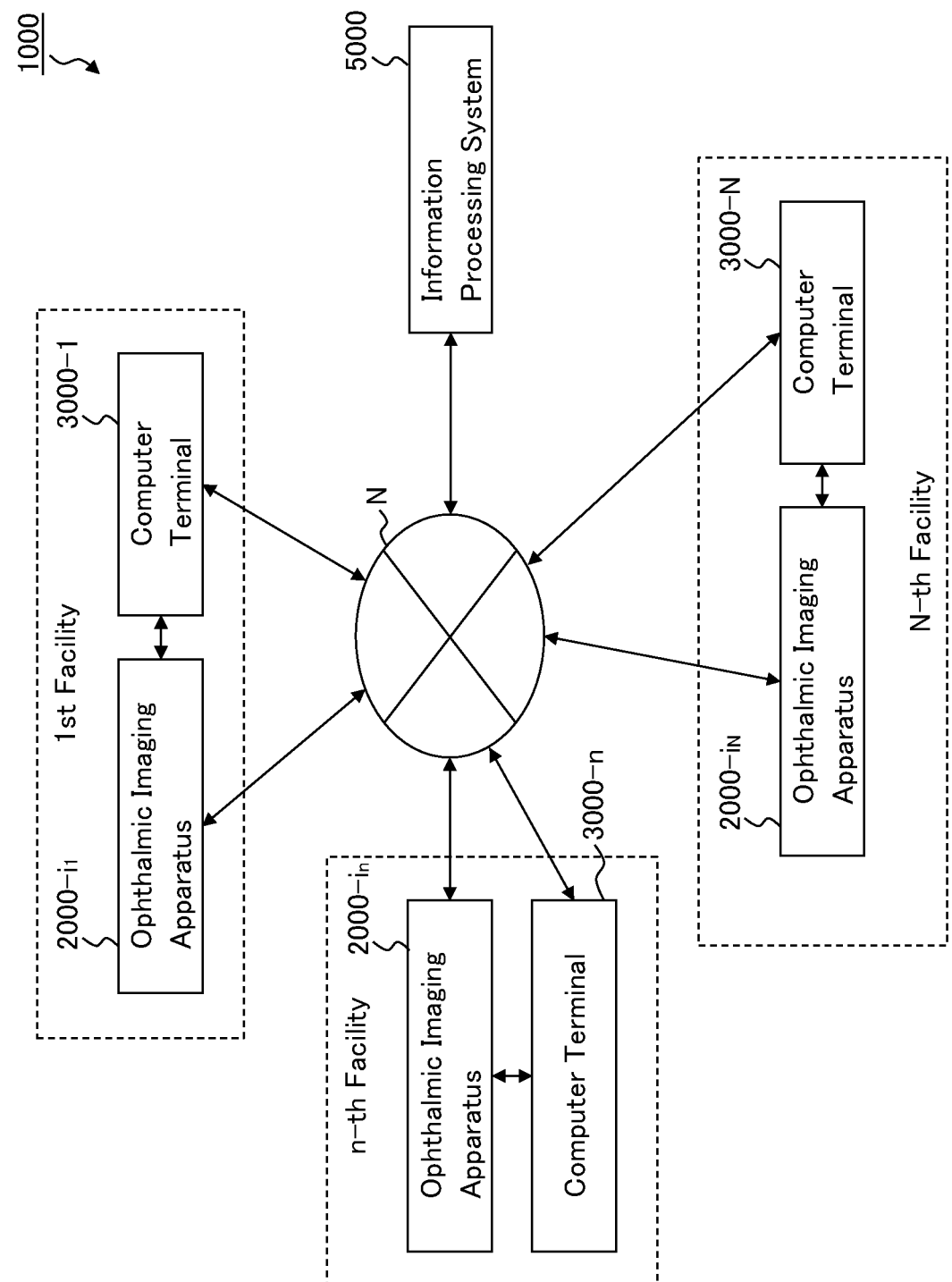
FIG. 1 is a schematic diagram illustrating an example of the configuration of the ophthalmic system according to the embodiment example.

Ophthalmic systems, ophthalmic information processing devices, and ophthalmic diagnosing methods according to some embodiment examples will be described in detail with referring to the drawings. It should be noted that any matter or item disclosed in the documents cited herein and any known technique or technology may be combined with the embodiment examples.

The ophthalmic system of some embodiments is configured to analyze, using an artificial intelligence technology and technique, an image acquired by an ophthalmic imaging apparatus installed in various kinds of facilities or by a portable ophthalmic imaging apparatus. The image analyzed is, in particular, a three dimensional image. The ophthalmic system of some embodiments includes a plurality of ophthalmic imaging apparatuses. The plurality of ophthalmic imaging apparatuses includes at least a plurality of slit lamp microscopes.

The plurality of ophthalmic imaging apparatuses may include modality apparatuses of a type(s) different from slit lamp microscopy. Examples of modality apparatuses applicable to some embodiments include an optical coherence tomography apparatus (OCT apparatus), a fundus camera, an SLO, and a surgical microscope (operation microscope). In addition, the plurality of ophthalmic imaging apparatuses may include an ophthalmic examination apparatus that includes an imaging apparatus for imaging a subject's eye. Examples of such ophthalmic examination apparatuses include a refractometer, a keratometer, a tonometer, a specular microscope, a wave front analyzer, a perimeter, and a microperimeter.

Examples of the facility in which the ophthalmic imaging apparatus is installed include a health facility, a medical institution, an optician's store, a health check and screening venue, a patient's home, a welfare facility, a public facility, an medical examination vehicle, and the like.

First Embodiment: Ophthalmic System

An example of the configuration of the ophthalmic system according to the embodiment will be described. The ophthalmic system 1000 illustrated in FIG. 1 as an embodiment example is configured by using a communication path (a communication line) N that connects each of N facilities (first to N-th facilities) at which ophthalmic imaging is conducted and the information processing system 5000.

Each of the facilities (n-th facility: where n=1 to N, N is any positive integer) is provided with the ophthalmic imaging apparatus $2000\text{-}i_n$ (where $i_n=1$ to $K_n$, $K_n$ is any positive integer). In other words, one or more ophthalmic imaging apparatuses $2000\text{-}i_n$ are installed in each of the facilities (n-th facility). The ophthalmic imaging apparatus $2000\text{-}i_n$ is included in the ophthalmic system 1000. Incidentally, the ophthalmic system 1000 may include an examination apparatus that is capable of performing examination other than ophthalmic examination.

The ophthalmic imaging apparatus $2000\text{-}i_n$ of the present example functions both as an "imaging apparatus" that conducts imaging of eyes, and as a "computer" that performs various kinds of data processing and communication with an external apparatus. For another example, an imaging apparatus and a computer may be provided separately from each other. If this is the case, the imaging apparatus and the computer may be configured to communicate with each other. There may be any number of imaging apparatuses and any number of computers. For example, a single computer and a plurality of imaging apparatuses may be provided.

Each of the facilities (n-th facility) is provided with an information processing apparatus used by an assistant or a subject (i.e., the computer terminal 3000-n). The computer terminal 3000-n is a computer for use in the corresponding facility. The computer terminal 3000-n may be, for example, a mobile computer terminal such as a tablet computer terminal or a smartphone, or a server installed in the corresponding facility. The computer terminal 3000-n may also include a wearable device such as a wireless earphone. It is only required that the computer terminal 3000-n is a computer capable of realizing its functions in the corresponding facility. Therefore, the computer terminal 3000-n may be, for example, a computer placed outside the corresponding facility such as a cloud server.

The ophthalmic imaging apparatus $2000\text{-}i_n$ and the computer terminal 3000-n may be configured to communicate with each other through a network such as a network built in the n-th facility (e.g., in-house LAN), a wide area network (e.g., the Internet). Alternatively, ophthalmic imaging apparatus $2000\text{-}i_n$ and the computer terminal 3000-n may be configured to communicate with each other using near-field communication technology.

The ophthalmic imaging apparatus $2000\text{-}i_n$ may be configured to function as a server. If this is the case, the ophthalmic imaging apparatus $2000\text{-}i_n$ and the computer terminal 3000-n may be configured to communicate directly with each other. This makes it possible for the information processing system 5000 and the computer terminal 3000-n to communicate with each other via the ophthalmic imaging apparatus $2000\text{-}i_n$, and thus the function of conducting communication between the computer terminal 3000-n and the information processing system 5000 becomes unnecessary.

The information processing system 5000 is provided in a facility for operating and managing the ophthalmic system 1, for example. The information processing system 5000 may communicate with at least one or more of the ophthalmic imaging apparatuses $2000\text{-}i_n$ installed in the first to N-th facilities, via the communication path N.

The information processing system 5000 may have a data processing function. For example, the information processing system 5000 may include a three dimensional image constructing unit that executes processing of constructing a three dimensional image from a plurality of cross sectional images of the subject's eye. The three dimensional image constructing unit includes a processor, a computer program, and the like.

Note that a "processor" as used in the present embodiment example is a circuit such as a central processing unit (CPU), a graphics processing unit (GPU), an application specific integrated circuit (ASIC), and a programmable logic device (PLD). Examples of the PLD include a simple programmable logic device (SPLD), a complex programmable logic device (CPLD), and a field programmable gate array (FPGA). For example, a processor in the present embodiment example is configured to load a program and/or data stored in a memory circuit or a storage device and execute processing based on the program and/or data, thereby implementing the functions according to the present embodiment example.

<Configuration of the Ophthalmic Imaging Apparatus>

A description is given of an example of the configuration of the ophthalmic imaging apparatus $2000\text{-}i_n$. The ophthalmic imaging apparatus $2000\text{-}i_n$ may be of any modality type as described above. The present embodiment example employs a slit lamp microscope as the ophthalmic imaging apparatus $2000\text{-}i_n$.

Here, the directions are defined. The front direction (or the depth direction) is defined as the direction towards the subject from the lens positioned closest to the subject (objective lens) in the optical system of the slit lamp microscope. The back direction is defined as the opposite direction of the front direction. The lateral direction (or the left and right direction) is defined as the horizontal direction orthogonal to the front direction. Further, the vertical direction (or the up and down direction) is defined as the direction orthogonal to both the front-back direction and the lateral direction.

Figure 2:
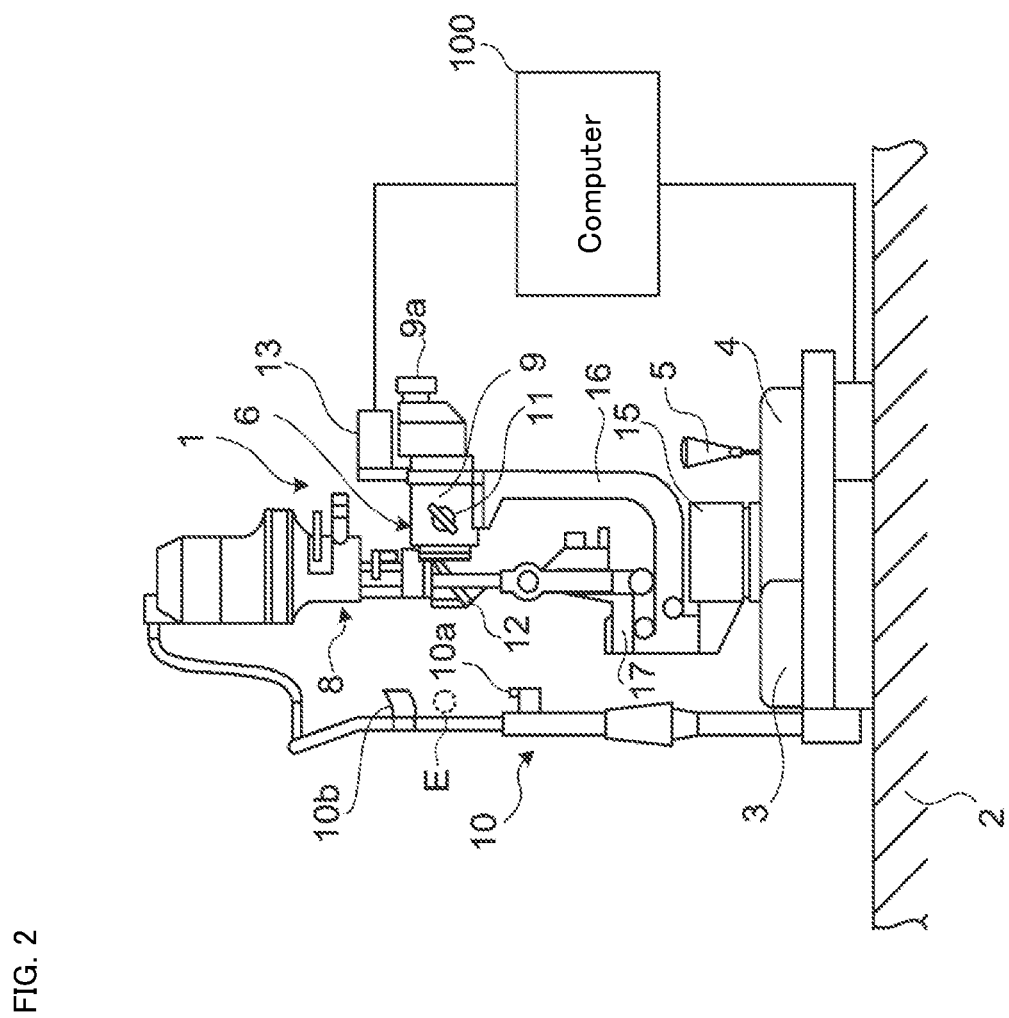
FIG. 2 is a schematic diagram illustrating an example of the configuration of the ophthalmic system according to the embodiment example.

FIG. 2 shows an example of the exterior configuration of the slit lamp microscope. The computer 100 is connected to the slit lamp microscope 1. The computer 100 executes various kinds of control processing and arithmetic processing. The configuration in which a computer like the computer 100 is provided in the main body of the microscope (housing thereof that stores optical systems etc.) may also be employed in place of providing the computer 100 separately from the main body of the microscope. At least part of the computer 100 and at least part of the aforementioned computer terminal 3000-n may be common.

The slit lamp microscope 1 is placed on the table 2. The base 4 is configured to be movable in the horizontal direction via the movement mechanism part 3. The base 4 is moved by tilting the operation handle 5.

The support portion 15 is provided on the upper surface of the base 4. The support portion 15 is configured to support the observation-photographing system 6 and the illumination system 8. The support arm 16 that supports the observation-photographing system 6 is attached to the support portion 15. The support arm 16 is rotatable (i.e., moving in a circular path) in the lateral direction. The support arm 17 that supports the illumination system 8 is attached to the upper portion of the support arm 16. The support arm 17 is rotatable in the lateral direction. The support arms 16 and 17 are independently rotatable in a coaxial manner with each other.

The observation-photographing system 6 is moved by the rotation of the support arm 16. The illumination system 8 is moved by the rotation of the support arm 17. Each of the support arms 16 and 17 is rotated by an electrical mechanism. The movement mechanism part 3 is provided with a mechanism for rotating the support arm 16 and a mechanism for rotating the support arm 17. The movement of the observation-photographing system 6 may be performed by manual rotation of the support arm 16. Likewise, the movement of the illumination system 8 may be performed by manual rotation of the support arm 17.

The illumination system 8 illuminates the subject's eye E with illumination light. As described above, the illumination system 8 may be rotated in the lateral direction. Further, the illumination system 8 may be rotatable in the vertical direction. In other words, the elevation angle and the depression angle of the illumination system 8 may be changeable. By such swinging motions of the illumination system 8, the projection direction of the illumination light with respect to the subject's eye E may be changed.

The observation-photographing system 6 includes a pair of left and right optical systems. Each of the left and right optical systems is configured to guide return light of the illumination light projected onto the subject's eye E. The left and right optical systems are stored in the body tube (or, lens tube, lens barrel, etc.) 9. The terminal end of the body tube 9 is the eyepiece portion 9a. The examiner observes the subject's eye E by looking into the eyepiece portion 9a. As described above, the body tube 9 may be rotated in the lateral direction by the rotation of the support arm 16. Further, the observation-photographing system 6 may be configured to be rotatable in the vertical direction. In other words, the elevation angle and the depression angle of the observation-photographing system 6 may be changeable. By such swinging motions of the observation-photographing system 6, the direction of photographing the subject's eye E may be changed.

The chin rest base 10 is disposed at a position facing the body tube 9. The chin rest base 10 is provided with the chin rest 10a and the forehead rest 10b for stably positioning the face of the subject.

The magnification operation knob 11 is disposed on the side surface of the body tube 9. The magnification operation knob 11 is operated to change the magnification. Furthermore, the imaging device 13 that captures an image of the subject's eye E is connected to the body tube 9. The imaging device 13 includes an image sensor. The image sensor is a photoelectric conversion element that detects light and outputs the image signal GS (electric signal). The image signal GS is input to the computer 100. The image sensor may be a charge-coupled device (CCD) image sensor or a complementary metal oxide semiconductor (CMOS) image sensor. The mirror 12 is disposed at the lower position of the illumination system 8. The mirror 12 redirects the illumination light beam output from the illumination system 8 toward the subject's eye E.

<Configuration of Optical Systems>

Figure 3:
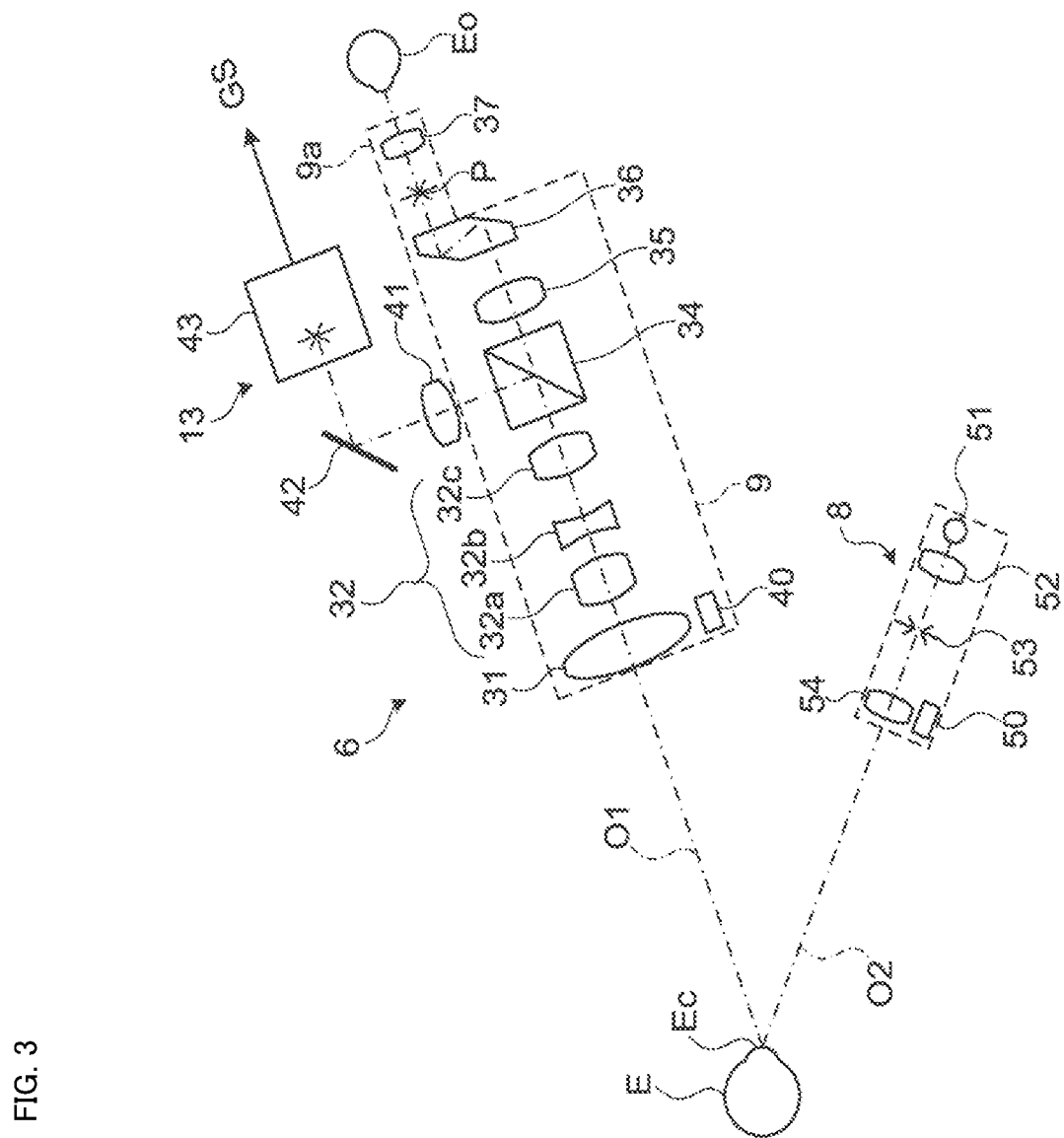
FIG. 3 is a schematic diagram illustrating an example of the configuration of the ophthalmic system according to the embodiment example.

FIG. 3 shows an example of the configuration of the optical systems of the slit lamp microscope 1. As described above, the slit lamp microscope 1 includes the observation-photographing system 6 and the illumination system 8.

<Observation-Photographing System 6>

The observation-photographing system 6 includes a pair of left and right optical systems. The left and right optical systems have almost the same configuration. The examiner may observe the subject's eye E with both eyes through the left and right optical systems. FIG. 3 shows only one of the left and right optical systems of the observation-photographing system 6. The observation-photographing system 6 may include only one of the left and right optical systems. The reference character O1 indicates the optical axis of the observation-photographing system 6.

Each of the left and right optical systems of the observation-photographing system 6 includes the objective lens 31, the variable magnification optical system (or zooming optical system) 32, the beam splitter 34, the imaging lens 35, the prism 36, and the eyepiece 37. Here, the beam splitter 34 is provided in one or both of the left and right optical systems. The eyepiece 37 is provided inside the eyepiece portion 9a. The reference character P indicates the imaging position of the light guided to the eyepiece 37. The reference character Ec indicates the cornea of the subject's eye E. The reference character Eo indicates the examiner's eye.

The variable magnification optical system 32 includes a plurality of (e.g., three) variable magnification lenses 32a, 32b, and 32c. In the present embodiment, a plurality of variable magnification lens groups is provided. The plurality of variable magnification lens groups is selectively inserted into the optical path of the observation-photographing system 6. The plurality of variable magnification lens groups respectively corresponds to magnifications differing from one another. One of the plurality of variable magnification lens groups selectively disposed in the optical path of the observation-photographing system 6 is used as the variable magnification optical system 32. The selective insertion of the plurality of variable magnification lens groups performed in this way makes it possible to change the magnification (angle of view) of the photographed image and the observation image of the subject's eye E. The change in the magnification, that is, the selection of the variable magnification lens group to be disposed in the optical path of the observation-photographing system 6, is performed by the operation of the magnification operation knob 11. Further, the configuration may be employed in which the magnification is changed electrically by using a switch (not shown in the drawings) or the like.

The beam splitter 34 splits the optical path of the light traveling along the optical axis O1 into an optical path located on the extension of the optical axis O1 and an optical path orthogonal to the optical axis O1. The light incident on the optical path located on the extension of the optical axis O1 is guided to the examiner's eye Eo via the imaging lens 35, the prism 36, and the eyepiece 37. The prism 36 translates the traveling direction of the light upward.

On the other hand, the light incident on the optical path orthogonal to the optical axis O1 is guided to the image sensor 43 of the imaging device 13 via the condenser lens 41 and the mirror 42. In other words, the observation-photographing system 6 guides the return light from the subject's eye E to the imaging device 13. The image sensor 43 detects the return light and generates the image signal GS.

The observation-photographing system 6 includes the focus mechanism 40 for changing the focal position of the observation-photographing system 6. The focus mechanism 40 moves the objective lens 31 along the optical axis O1. For example, the focus mechanism 40 includes a holding member that holds the objective lens 31, a sliding mechanism that moves the holding member in the direction along the optical axis O1, an actuator that generates a driving force, and a member that transmits the driving force to the sliding mechanism.

The movement of the objective lens 31 is carried out automatically and/or manually. In the case where automatic movement of the objective lens 31 is employed, for example, the computer 100 may determine the focal position based on the return light from the subject's eye E using a known focus adjustment method (e.g., a phase difference detection method, or a contrast detection method). Further, the computer 100 may control the actuator to move the objective lens 31 along the optical axis O1 to the focal position determined. On the other hand, in the case where manual movement of the objective lens 31 is employed, the actuator moves the objective lens 31 along the optical axis O1 according to an operation performed by the user.

The observation-photographing system 6 may include a first focusing lens that is disposed at a position on the optical axis O1 between the objective lens 31 and the image sensor 43. When the first focusing lens is included, the focus mechanism 40 changes the focal position of the observation-photographing system 6 by moving the first focusing lens along the optical axis O1. For example, the focus mechanism 40 includes a holding member that holds the first focusing lens, a sliding mechanism that moves the holding member in the direction along the optical axis O1, an actuator that generates a driving force, and a member that transmits the driving force to the sliding mechanism. As in the case where the objective lens 31 is moved, the movement of the first focusing lens with the focus mechanism 40 is carried out automatically or manually.

Further, the entire (or, part of the) observation-photographing system 6 may be configured to be movable along the optical axis O1. If this is the case, the focus mechanism 40 changes the focal position of the observation-photographing system 6 by moving the entire (or, part of the) observation-photographing system 6 along the optical axis O1. For example, the focus mechanism 40 includes a movable stage on which the entire (or, part of the) observation-photographing system 6 is placed, a sliding mechanism that moves the movable stage in the direction along the optical axis O1, an actuator that generates a driving force, and a member that transmits the driving force to the sliding mechanism. As in the case where the objective lens 31 is moved, the movement of the observation-photographing system 6 with the focus mechanism 40 is carried out automatically or manually.

<Illumination System 8>

The illumination system 8 includes the illumination light source 51, the condenser lens 52, the slit forming part 53, and the objective lens 54. The reference character O2 indicates the optical axis of the illumination system 8.

The illumination light source 51 outputs illumination light. The illumination system 8 may include a plurality of light sources. For example, the illumination light source 51 may include both a light source that outputs steady light or continuous light and a light source that outputs flash light. Examples of the light source that outputs steady light or continuous light include a halogen lamp and a light emitting diode (LED). Examples of the light source that outputs flash light include a xenon lamp and an LED. The illumination light source 51 may include a light source for the observation of anterior eye segment and another light source for the observation of posterior eye segment. For example, the illumination light source 51 includes a visible light source that outputs visible light. The illumination light source 51 may also include an infrared light source that outputs infrared light. The center wavelength of the infrared light is, for example, a value between 800 nm and 1000 nm.

The slit forming part 53 is used to generate slit light. The slit forming part 53 has a pair of slit blades. The width of the slit light to be generated may be changed by changing the interval between the slit blades. The interval between the slit blades is called slit width.

The illumination system 8 includes the focus mechanism 50 for changing the focal position of the slit light. The focus mechanism 50 moves the objective lens 54 along the optical axis O2. For example, the focus mechanism 50 includes a holding member that holds the objective lens 54, a sliding mechanism that moves the holding member in the direction along the optical axis O1, an actuator that generates a driving force, and a member that transmits the driving force to the sliding mechanism.

The movement of the objective lens 54 is carried out automatically and/or manually. In the case where the automatic movement of the objective lens 54 is employed, for example, the computer 100 may determine the focal position by analyzing an image that depicts the image corresponding to the return light from the subject's eye E. Further, the computer 100 may control the actuator to move the objective lens 54 along the optical axis O2 to the focal position determined. On the other hand, in the case where manual movement of the objective lens 54 is employed, the actuator moves the objective lens 54 along the optical axis O2 according to an operation performed by the user.

The illumination system 8 may include a second focusing lens that is disposed at a position in the optical axis O2 between the objective lens 54 and the slit forming part 53. When the second focusing lens is included, the focus mechanism 50 changes the focal position of the slit light by moving the second focusing lens along the optical axis O2. For example, the focus mechanism 50 includes a holding member that holds the second focusing lens, a sliding mechanism that moves the holding member in the direction along the optical axis O2, an actuator that generates a driving force, and a member that transmits the driving force to the sliding mechanism. As in the case where the objective lens 54 is moved, the movement of the second focusing lens with the focus mechanism 50 is carried out automatically or manually.

Further, the entire (or, part of the) illumination system 8 may be configured to be movable along the optical axis O2. If this is the case, the focus mechanism 50 changes the focal position of the slit light by moving the entire (or, part of the) illumination system 8 along the optical axis O2. For example, the focus mechanism 50 includes a movable stage on which the illumination system 8 is placed, a sliding mechanism that moves the movable stage in the direction along the optical axis O2, an actuator that generates a driving force, and a member that transmits the driving force to the sliding mechanism. As in the case where the objective lens 54 is moved, the movement of the illumination system 8 with the focus mechanism 50 is carried out automatically or manually.

Although not shown in FIG. 3, the mirror 12 is disposed in the optical axis O2. The mirror 12 redirects the illumination light beam output from the illumination system 8 toward the subject's eye E. Typically, the illumination system 8 and the mirror 12 are configured to be capable of rotating together.

The slit lamp microscope 1 may acquire a plurality of images by photographing the subject's eye E multiple times in parallel with performing the changes in the illumination angle and the photographing angle with respect to the subject's eye E. In other words, the slit lamp microscope 1 may acquire a plurality of cross sectional images of the subject's eye E by photographing the subject's eye E multiple times in parallel with performing the rotation of the illumination system 8 and the rotation of the observation-photographing system 6.

To each of the plurality of cross sectional images acquired through such control, position information indicating the corresponding acquisition position (e.g., corresponding cross sectional position) is assigned. For example, the position information may include any one or more of the followings: the rotational position of the illumination system 8; the rotational position of the observation-photographing system 6; the position of the cross section in the front image of the subject's eye E; and information created based on any of these.

The rotational position of the illumination system 8 and/or the rotational position of the observation-photographing system 6 may be detected, for example, with a rotational position detector including an encoder or the like. Alternatively, the rotational position of the illumination system 8 and/or the rotational position of the observation-photographing system 6 may be recognized by the computer 100 that controls the rotations. Further, the position of the cross section in the front image of the subject's eye E may be determined based on, for example, another front image of the subject's eye E and the result of detection obtained by the rotational position detector. A three dimensional image of the subject's eye E may be constructed from such position information and the plurality of cross sectional images. Details of this processing will be described later.

It is to be noted that the plurality of times of photography of the subject's eye E carried out in parallel with performing the changes in the illumination angle and the photographing angle may be conducted while the illumination angle and/or the photographing angle are/is changing, or while the change(s) in the illumination angle and/or the photographing angle are/is being stopped. Further, the change in the illumination angle may be in a continuous or intermittent manner. The change in the photographing angle may also be in a continuous or intermittent manner.

The slit lamp microscope 1 may acquire a plurality of images by photographing the subject's eye E multiple times in parallel with performing the change in the focal position with respect to the subject's eye E. More specifically, the slit lamp microscope 1 may acquire a plurality of cross sectional images of the subject's eye E by photographing the subject's eye E multiple times in parallel with performing at least one of the change in the focal position of the observation-photographing system 6 and the change in the focal position of the illumination system 8.

To each of the plurality of cross sectional images acquired through such control, position information indicating the corresponding acquisition position (e.g., corresponding focal position) is assigned. The position information may include any one or more of the followings: the contents of control for the focus mechanism 40; the contents of control for the focus mechanism 50; the position of an object (e.g., the objective lens 31, the first focusing lens, or the observation-photographing system 6) to be moved by the focus mechanism 40; the position of an object (e.g., the objective lens 54, the second focusing lens, or the illumination system 8) to be moved by the focus mechanism 50; and information created based on any of these.

The control contents for the focus mechanism 40 or 50 may be recognized, for example, by the computer 100 that controls the focus mechanism 40 or 50. The position of the object to be moved by the focus mechanism 40 or 50 may be detected, for example, by a position detector including an encoder or the like. A three dimensional image of the subject's eye E may be constructed from such position information and the plurality of cross sectional images. Details of this processing will be described later.

It is to be noted that the plurality of times of photography of the subject's eye E carried out in parallel with performing the change in the focal position may be performed while the focal position is changing, as well as while the change in the focal position is being stopped. Further, the change in the focal position may be in a continuous or intermittent manner.

The two kinds of controls described above may be combined. More specifically, the slit lamp microscope 1 may acquire a plurality of cross sectional images by photographing the subject's eye E multiple times in parallel with performing the changes in the illumination angle, the photographing angle, and the focal position. To each of the plurality of cross sectional images acquired through the combined control, position information indicating the corresponding acquisition positions (cross sectional position and focal position) is assigned.

<Configuration of Control System>

Figure 4:
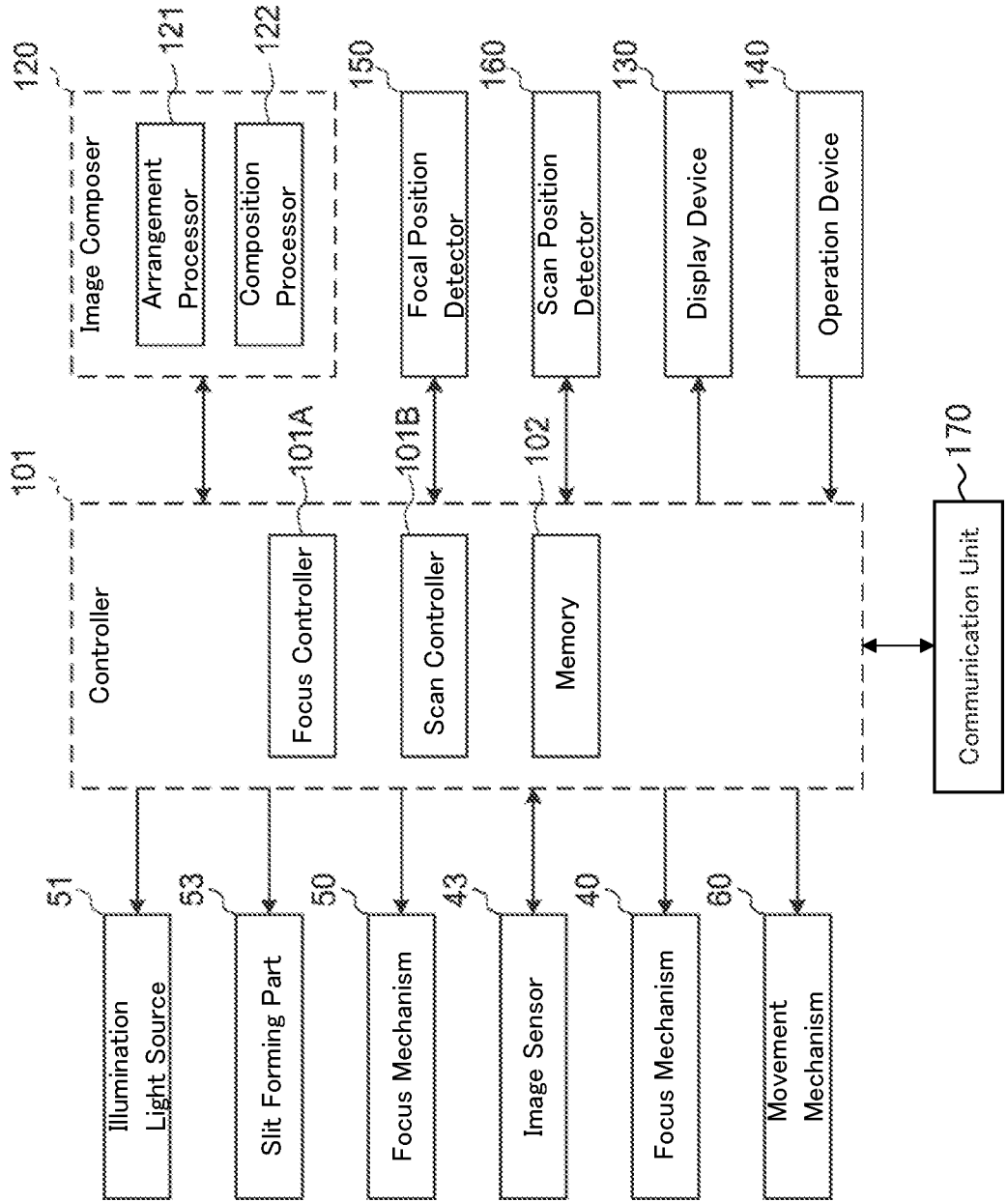
FIG. 4 is a schematic diagram illustrating an example of the configuration of the ophthalmic system according to the embodiment example.
Figure 5:
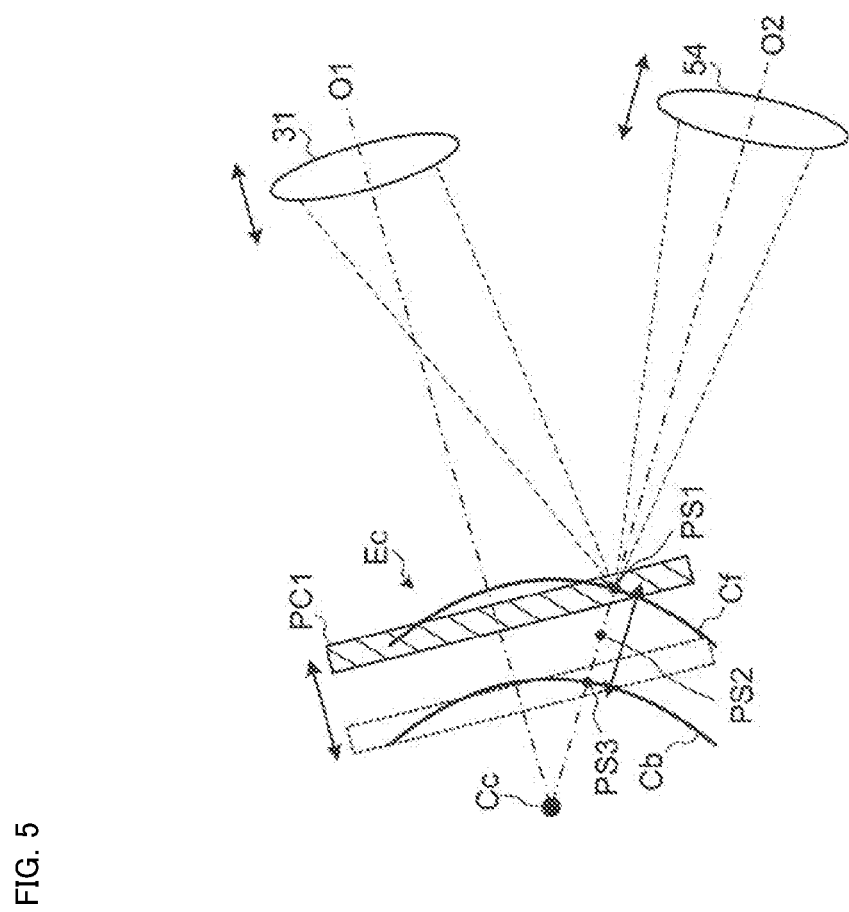
FIG. 5 is a schematic diagram for describing an example of the operation of the ophthalmic system according to the embodiment example.
Figure 6:
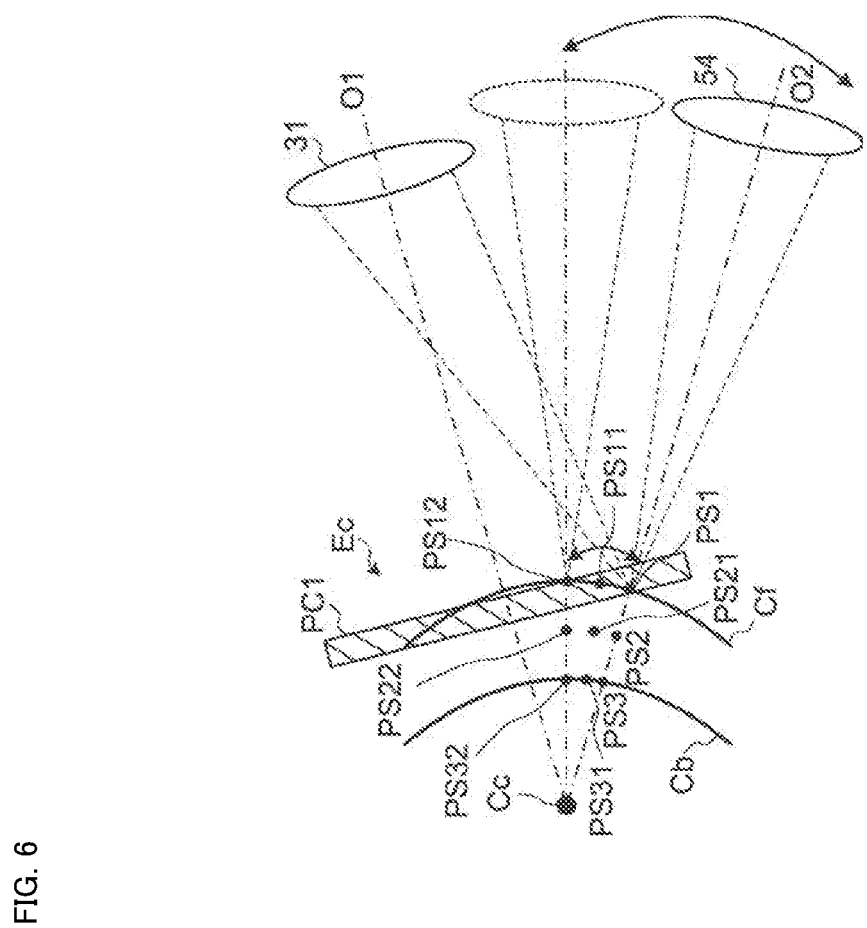
FIG. 6 is a schematic diagram for describing an example of the operation of the ophthalmic system according to the embodiment example.

The control system of the slit lamp microscope 1 will be described with referring to FIG. 4 to FIG. 6. FIG. 4 shows an example of the configuration of the control system of the slit lamp microscope 1. Note that the computer 100 may include at least part of a plurality of elements constituting the control system.

<Controller 101>

The controller 101 controls each part of the slit lamp microscope 1. The controller 101 controls the observation-photographing system 6, the illumination system 8, the display device 130, the communication unit 170, etc.

The controls for the observation-photographing system 6 may include any one or more of the followings: control for the variable magnification optical system 32; control for the image sensor 43; control for the focus mechanism 40; control for the movement mechanism 60 that moves the observation-photographing system 6; control for the focal position detector 150; and control for the scan position detector 160. The control for the variable magnification optical system 32 may include the control to change the magnification (magnification ratio) of an observation image or a photographed image of the subject's eye E in accordance with the content of an operation performed using the magnification operation knob 11. The control for the image sensor 43 may include any of the followings: the control to change the electric charge accumulation time, the sensitivity, the frame rate, etc. of the image sensor 43; and the control to send the image signal GS generated by the image sensor 43 to the image composer 120. The control for the focus mechanism 40 may include the control to change the focal position of the observation-photographing system 6. The movement mechanism 60 may include, for example, the movement mechanism part 3, the support arms 16 and 17, and a mechanism that moves the support arms 16 and 17. The control for the movement mechanism 60 may include the control to rotate the observation-photographing system 6. The control for the focal position detector 150 may include the control to acquire the position detected by the focal position detector 150 and send the acquired position to the image composer 120. The control for the scan position detector 160 may include the control to acquire the position detected by the scan position detector 160 and send the acquired position to the image composer 120.

The controls for the illumination system 8 may include the followings: control for the illumination light source 51; control for the slit forming part 53; control for the focus mechanism 50; control for the movement mechanism 60 for moving the illumination system 8; control for the focal position detector 150; and control for the scan position detector 160. The control for the illumination light source 51 may include the control to switch on and off the illumination light source 51, and the control to change the quantity of the illumination light. The control for the slit forming part 53 may include the control to change the slit width, the control to translate the slit, and the control to rotate the slit. The control for the focus mechanism 50 may include the control to change the focal position of the slit light (focal position of the illumination system 8). The control for the movement mechanism 60 may include the control to move the illumination system 8. The control for the focal position detector 150 may include the control to acquire the position detected by the focal position detector 150 and send the acquired position to the image composer 120. The control for the scan position detector 160 may include the control to acquire the position detected by the scan position detector 160 and send the acquired position to the image composer 120.

The controller 101 includes the focus controller 101A, the scan controller 101B, and the memory 102.

The focus controller 101A executes the control for the focal position of the observation-photographing system 6 and the control for the focal position of the illumination system 8.

The controls carried out by the focus controller 101A will be described with referring to FIG. 5. FIG. 5 schematically shows the focal positions of the observation-photographing system 6 and the illumination system 8 with respect to the cornea Ec of the subject's eye E. As described above, the reference character 31 indicates the objective lens of the observation-photographing system 6, and the reference character 54 indicates the objective lens of the illumination system 8. The reference character Cf indicates the front surface of the cornea Ec, and the reference character Cb indicates the back surface of the cornea Ec. The reference character Cc indicates the position of the center of curvature of the cornea Ec (the position of the center of curvature of the front surface Cf). For example, the rotation axis of the observation-photographing system 6 and that of the illumination system 8 both substantially coincide with the curvature center position Cc.

The focus controller 101A controls a scan in the depth direction with respect to the interested site of the subject's eye E. The depth direction with respect to the interested site corresponds to the radial direction in the rotational operation. Such a scan is called an r-scan. The focus controller 101A may execute the control of the focus mechanism 40 and the control of the focus mechanism 50 in an interlocking manner. For example, the focus controller 101A controls the focus mechanism 40 and the focus mechanism 50 to direct the focal position of the observation-photographing system 6 and the focal position of the illumination system 8 at the positions PS1, PS2 and PS3 in this order. The positions PS1, PS2 and PS3 are arranged along the depth direction of the interested site, that is, along the depth direction in the subject's eye E. The observation-photographing system 6 may perform photography of the subject's eye E with depths of field respectively corresponding to the focal positions applied. For example, the observation-photographing system 6 may capture an image of the subject's eye E in the depth of field PC1 corresponding to the position PS1.

The focus controller 101A may execute the control for the imaging device 13 to capture an image and the interlocking control described above in an alternate manner. With this, the focus controller 101A may control the acquisition of a plurality of cross sectional images arranged in the depth direction of the interested site of the subject's eye E. For example, the focus controller 101A may perform the control in such a way that an image of a cross section including the position PS1, an image of a cross section including the position PS2, and an image of a cross section including the position PS3 are sequentially captured.

The scan controller 101B performs the control to move the scan position with respect to the interested site of the subject's eye E in the horizontal direction (i.e., in the direction substantially orthogonal to the depth direction). Although detailed description is omitted, the control to move the scan position in the vertical direction may also be executed in the same manner. Here, the vertical direction is substantially orthogonal to both the horizontal direction and the depth direction.

The operation of the scan controller 101B will be described with referring to FIG. 6. FIG. 6 schematically shows the focal positions of the observation-photographing system 6 and the illumination system 8 with respect to the cornea Ec. In FIG. 6, parts, sites, elements, etc. similar to those in FIG. 5 are indicated by the same reference characters, and descriptions thereof are omitted unless otherwise stated.

The scan controller 101B controls a scan in the horizontal direction with respect to the interested site of the subject's eye E. The horizontal direction with respect to the interested site corresponds to the angle direction in the rotational operation. Such a scan is called a θ-scan. The scan controller 101B may execute the control of the movement mechanism 60 so as to interlock the rotation of the illumination system 8 and the rotation of the observation-photographing system 6 with each other. For example, the scan controller 101B moves the observation-photographing system 6 and the illumination system 8 in the order of the scan positions PS1, PS11, and PS12 in the horizontal direction.

The scan controller 101B may execute the control for the imaging device 13 to capture an image and the control for the movement mechanism 60 in an alternate manner. With this, the scan controller 101B may execute control for acquisition of a plurality of cross sectional images arranged in the horizontal direction in the interested site of the subject's eye E. For example, the scan controller 101B may conduct control in such a way that an image of a cross section including the position PS1, an image of a cross section including the position PS11, and an image of a cross section including the position PS12 are sequentially captured.

At each of the positions PS1, PS11, and PS12 in the horizontal direction, the focus controller 101A may change the focal position of the observation-photographing system 6 and the focal position of the illumination system 8 in the depth direction. As a result of this, one or more cross sectional images may be acquired for each of the positions PS1, PS2, PS3, PS11, PS21, PS31, PS12, PS22, and PS32.

The memory 102 is configured to store various kinds of computer programs and data. The computer programs include an arithmetic program and a control program for operating the slit lamp microscope 1 according to a predetermined operation mode. The data includes various kinds of data used in various kinds of examinations. Scan information is an example of such data. For example, the scan information includes the followings: control information for moving the observation-photographing system 6 and the illumination system 8 to a plurality of scan positions of the interested site; and control information for changing the focal position of the observation-photographing system 6 and that of the illumination system 8 to one or more positions in the depth direction corresponding to scan positions. These pieces of control information are stored in the memory 102 in advance. By using the computer programs and the scan information stored in the memory 102, the controller 101 may execute the control of the scan controller 101B to move the scan position in the horizontal direction and the control of the focus controller 101A to move the focal position, in an individual manner or in an interlocking manner.

One or more operation modes may be provided in advance for the slit lamp microscope 1. The present embodiment may be provided with a three dimensional imaging mode. The three dimensional imaging mode is an operation mode for acquiring three dimensional images of the subject's eye. In the three dimensional imaging mode, the controller 101 of the slit lamp microscope 1 controls the illumination system 8, the observation-photographing system 6, the movement mechanism 60, and the focus mechanisms 40 and 50 in an interlocking manner so that the imaging device 13 acquires a plurality of cross sectional images of the subject's eye E. Note that the operation modes of the slit lamp microscope 1 are not limited to the three dimensional imaging mode.

An operation mode is designated using, for example, the computer terminal 3000-n or the operation device 140 of the slit lamp microscope 1. Alternatively, an operation mode may be designated using a device connectable to the slit lamp microscope 1 via the communication path N. For example, an operation mode may be designated using a computer used by a doctor in a remote site.

The aspects of the operation mode designation are not limited to such manual designation. For example, an operation mode that had been applied to the concerned subject in the past may be obtained from an electronic medical record or the like and the operation mode applied in the past may be designated again. In addition, an operation mode associated in advance with a specific disease may be automatically designated. Further, an operation mode associated in advance with a specific type of examination (e.g., screening, health check, health examination, general examination, medical consultation) may be automatically designated.

The controller 101 includes a processor, a random access memory (RAM), a read only memory (ROM), a hard disk drive, etc. Control programs are stored in advance in a storage such as the ROM and the hard disk drive. The operation of the controller 101 is implemented through cooperation of software such as the control programs and hardware such as the processor. The controller 101 is disposed in the main body of the slit lamp microscope 1 (e.g., inside the base 4) or in the computer 100.

<Image Composer 120>

The image composer 120 is configured to compose a plurality of cross sectional images acquired by the imaging device 13 according to the above-described control executed by the focus controller 101A and/or the scan controller 101B.

For example, the image composer 120 composes a plurality of cross sectional images acquired by the imaging device 13 while the focus mechanism 40 and the focus mechanism 50 have been changing the respective focal positions. In this case, the plurality of cross sectional images is arranged in the depth direction. In other words, the plurality of cross sections corresponding to the plurality of cross sectional images is lain in the same plane. A composite image constructed from such cross sectional images is a two dimensional cross sectional image with a depth of field that is deeper than those of individual cross sectional images. In other words, such a composite image is a pan-focus (or deep focus) two dimensional cross sectional image.

The image composer 120 may compose a plurality of (two dimensional) cross sectional images whose respective cross sections are not lain in the same plane, to construct a three dimensional image. Note that a three dimensional image refers to an image (image data) whose pixel positions are defined by a three dimensional coordinate system.

Stack data of a plurality of cross sectional images is an example of three dimensional images. The stack data is image data constructed by arranging a plurality of cross sectional images obtained at a plurality of differing scan positions in a three dimensional manner, based on the positional relationship of the scan positions. More specifically, the stack data is image data constructed by representing a plurality of cross sectional images, which are originally defined by individual two dimensional coordinate systems, by a single three dimensional coordinate system. That is, the stack data is image data constructed by embedding a plurality of cross sectional images in a single three dimensional space.

Volume data is another example of three dimensional images. The volume data is also referred to as voxel data. The volume data is image data in which voxels, which are three dimensional picture elements, are arranged in a three dimensional manner. The volume data is constructed, for example, by applying interpolation to stack data and three-dimensionalize (or voxelize) the pixels of the stack data interpolated.

In order to execute the image composition processing described above, the image composer 120 includes the arrangement processor 121 and the composition processor 122.

The arrangement processor 121 is configured to determine the arrangement of a plurality of cross sectional images acquired by the aforementioned r-scan, θ-scan, or a combination of the r-scan and the θ-scan, based on a plurality of pieces of position information (e.g., focal positions, cross sectional positions) associated with the plurality of cross sectional images. In addition, the arrangement processor 121 is configured to place the plurality of cross sectional images in accordance with the arrangement determined.

For example, the arrangement processor 121 receives focal positions of the slit light detected by the focal position detector 150 (e.g., the position information described above) from the controller 101, and then places the plurality of cross sectional images according to the focal positions received. As another example, the arrangement processor 121 receives, from the controller 101, rotational positions of the observation-photographing system 6 and the illumination system 8 detected by the scan position detector 160 (e.g., the position information described above), and then places the plurality of cross sectional images according to the rotational positions received.

The composition processor 122 is configured to compose the plurality of cross sectional images arranged by the arrangement processor 121. This image composition processing may include, for example, a process of constructing stack data, and may further include a process of constructing volume data from the stack data.

By executing a series of processes described above, the image composer 120 is capable of constructing a three dimensional image or a two dimensional image from a plurality of cross sectional images of the subject's eye E.

In another example, the image composer 120 may compose a plurality of cross sectional images without using the position information described above. For example, the image composer 120 may be configured to execute the following processes: a process of applying image analysis to a plurality of cross sectional images to determine two or more image regions, all of which correspond to the same site of the subject's eye E, in two or more cross sectional images (the image regions are called common regions); and a process of composing (or pasting together) the two or more cross sectional images in such a manner that the common regions overlap with each other. In the case where the image analysis described above is employed, the focal position detector 150 and/or the scan position detector 160 are not required. On the other hand, the image composer 120 may be configured to first perform rough position adjustment (rough registration) of images on the basis of information obtained by the focal position detector 150 and/or the scan position detector 160, and then perform further registration using the image analysis.

At least part of the functions of the image composer 120 may be installed in an apparatus different from the slit lamp microscope 1. For example, a computer that is capable of communicating with the slit lamp microscope 1 may have at least part of the functions of the image composer 120. As a specific example, a computer located in the facility where the slit lamp microscope 1 is installed (e.g., the computer terminal 3000-n, an intra-facility server, or the like) may have at least part of the functions of the image composer 120. Alternatively, the information processing system 5000 or a computer that is capable of communicating with the information processing system 5000 may have at least part of the functions of the image composer 120.

<Focal Position Detector 150>

The focal position detector 150 includes, for example, the first focal position detector and the second focal position detector. The first focal position detector is configured to detect the focal position of the observation-photographing system 6, and the second focal position detector is configured to detect the focal position of the illumination system 8. The first focal position detector and/or the second focal position detector may include a position sensor such as an encoder or a potentiometer.

In another example, the first focal position detector may include a processor configured to determine the focal position of the observation-photographing system 6 based on the contents of controls executed by the focus controller 101A for the observation-photographing system 6. Here, the contents of the controls correspond to the history of the controls. Likewise, the second focal position detector may include a processor configured to determine the focal position of the illumination system 8 based on the contents of controls executed by the focus controller 101A for the illumination system 8 (i.e., based on the history of the controls).

<Scan Position Detector 160>

The scan position detector 160 includes, for example, the first position detector and the second position detector. The first position detector is configured to detect the position of the observation-photographing system 6, and the second position detector is configured to detect the position of the illumination system 8. The first position detector and/or the second position detector includes, for example, a position sensor configured to detect the position of the base 4, and a rotation angle sensor(s) configured to detect the positions of the support arms 16 and 17.

In another example, the first position detector may include a processor configured to determine the position of the observation-photographing system 6 based on the contents of controls (i.e., the history of controls) executed by the scan controller 101B for the observation-photographing system 6. Likewise, the second position detector may include a processor configured to determine the position of the illumination system 8 based on the contents of controls (i.e., the history of controls) executed by the scan controller 101B for the illumination system 8.

<Display Device 130>

The display device 130 is configured to display various kinds of information under the control of the controller 101. For example, the display device 130 includes a flat panel display such as a liquid crystal display (LCD). The display device 130 may be provided on the main body of the slit lamp microscope 1 or may be provided in the computer 100.

<Operation Device 140>

The operation device 140 includes an operation device for operating the slit lamp microscope 1 and an input device for inputting information. The operation device 140 includes buttons and switches provided in the slit lamp microscope 1

(e.g., the operation handle 5, the magnification operation knob 11, and the like), and operation devices provided in the computer 100 (e.g., a mouse, a keyboard, and the like). Further, the operation device 140 may include any kinds of operation devices and any kinds of input devices, such as a trackball, an operation panel, a switch, a button, and a dial.

The display device 130 and the operation device 140 are separated in FIG. 4; however, at least part of the display device 130 and at least part of the operation device 140 may be the same device. A touch screen is a specific example of such a device.

<Communication Unit 170>

The communication unit 170 is configured to perform data communication between the slit lamp microscope 1 and another apparatus. The data communication system employed herein is arbitrary. For example, the communication unit 170 may include any one or more of a communication interface conforming to the Internet, a communication interface conforming to a dedicated line, a communication interface conforming to LAN, and a communication interface conforming to near field communication. The data communication may be either wireless communication or wired communication.

Data sent and received by the communication unit 170 may be encrypted. If this is the case, for example, the controller 101 includes an encryptor and a decryptor. The encryptor is configured to encrypt data to be sent. The decryptor is configured to decrypt received data.

<Information Processing System 5000>

Figure 7:
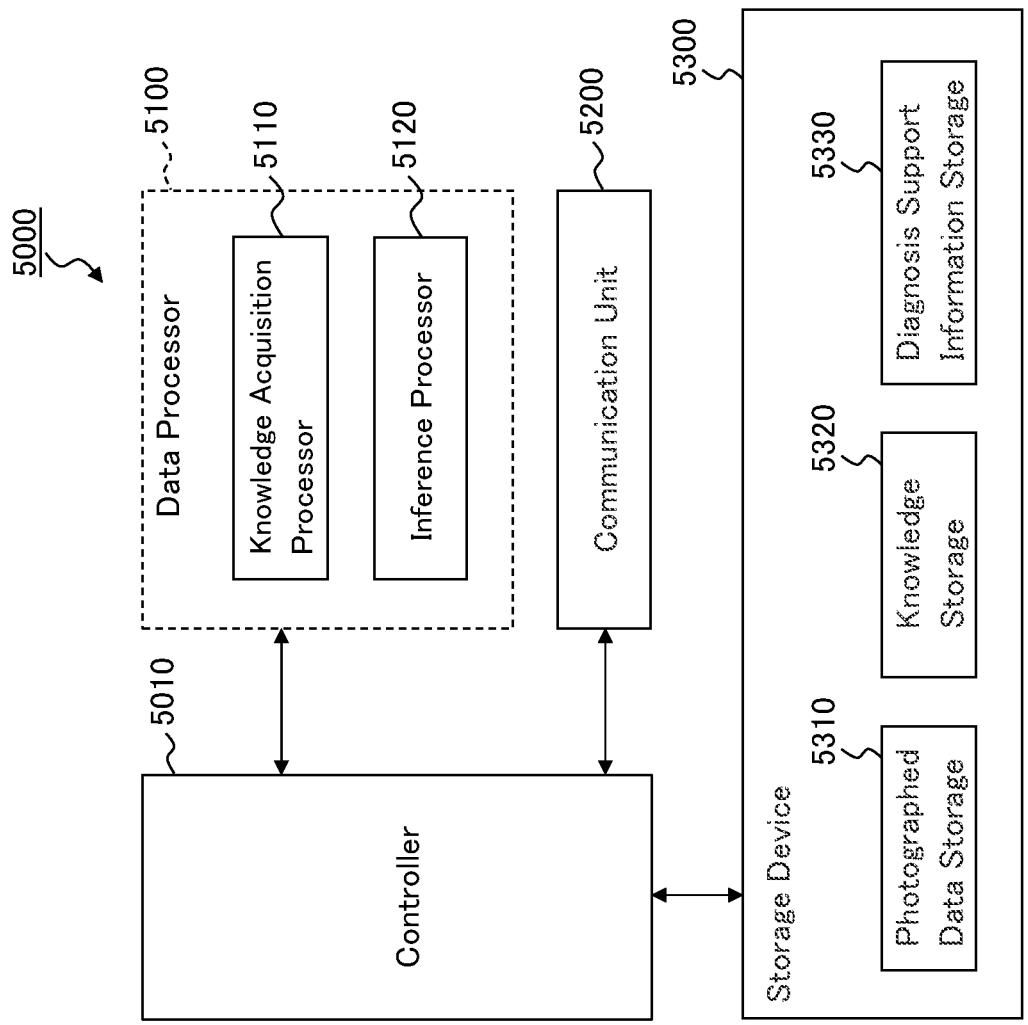
FIG. 7 is a schematic diagram illustrating an example of the configuration of the ophthalmic system according to the embodiment example.

The configuration of the information processing system 5000 will be described. The information processing system 5000 shown in FIG. 7 includes the controller 5010, the data processor 5100, the communication unit 5200, and the storage device 5300.

<Controller 5010>

The controller 5010 is configured to execute control of each part of the information processing system 5000. The controller 5010 may be capable of executing other processing such as arithmetic processing. The controller 5010 includes a processor, a RAM, a ROM, a hard disk drive, a solid state drive, etc.

<Data Processor 5100>

The data processor 5100 is configured to execute various kinds of data processing. The data processor 5100 includes a processor, a RAM, a ROM, a hard disk drive, a solid state drive, etc.

The data processor 5100 may have the function of constructing a three dimensional image (e.g., stack data or volume data) from a plurality of cross sectional images transmitted from the slit lamp microscope 1 (the ophthalmic imaging apparatus $2000\text{-}i_n$). Further, the data processor 5100 may have a function of constructing volume data from stack data transmitted from the slit lamp microscope 1 (the ophthalmic imaging apparatus $2000\text{-}i_n$).

The data processor 5100 may have a rendering function. For example, the data processor 5100 may perform rendering on a three dimensional image constructed by the ophthalmic imaging apparatus $2000\text{-}i_n$ or the like. A rendering method employed herein is arbitrary. For example, the rendering may include three dimensional computer graphics. The three dimensional computer graphics is arithmetic processing to construct an image having a stereoscopic effect by converting a virtual three dimensional object (e.g., a three dimensional image such as stack data or volume data) in a three dimensional space defined by a three dimensional coordinate system, into two dimensional information. Examples of the rendering include the volume rendering method, the maximum intensity projection method (MIP), the minimum intensity projection method (MinIP), the surface rendering method, the multi planar reconstruction method (MPR), the projection image construction, and the shadowgram construction.

The data processor 5100 includes the knowledge acquisition processor 5110 and the inference processor 5120. The knowledge acquisition processor 5110 and/or the inference processor 5120 are/is capable of processing at least one of the following information, for example: a three dimensional image constructed by the ophthalmic imaging apparatus $2000\text{-}i_n$ or the like; a rendered image of a three dimensional image; analysis data of a three dimensional image; analysis data of a rendered image; and other information (e.g., any medical information such as subject information, a front image, electronic medical record information, an interpretation report, etc.).

<Knowledge Acquisition Processor 5110>

The knowledge acquisition processor 5110 is configured to acquire knowledge by executing at least one of machine learning and data mining based on data collected in advance. The data collected in advance is stored in the photographed data storage 5310 of the storage device 5300.

The data collection is performed using, for example, any one or more of the ophthalmic imaging apparatuses $2000\text{-}i_n$, other ophthalmic imaging apparatuses, ophthalmic examination apparatuses, and apparatuses used in other medical departments such as the radiology department. Further, information input by doctors (e.g., electronic medical records, interpretation reports, or the like) may also be collected.

Furthermore, the data used for machine learning and/or data mining may include any medical knowledge, knowledge in other academic fields, knowledge in any fields other than academic fields. Such knowledge may include, for example, any of the followings: knowledge based on specialized books (e.g., medical books); knowledge based on articles (e.g., medical treatises); knowledge based on information generated by public organizations or private organizations (e.g., clinical practice guidelines); knowledge based on dictionaries (e.g., medical dictionaries); knowledge based on corpora (e.g. medical corpora); knowledge based on knowledge bases (e.g., medical knowledge bases); knowledge obtained by other machine learning; knowledge obtained by other data mining; knowledge obtained by information and/or method other than the above knowledge items or matters; and knowledge obtained from combinations of any two or more of the above knowledge items or matters.

In addition, the data used for machine learning and/or data mining may include information and/or data used to obtain the knowledge of the types described above. For example, the data used for machine learning and/or data mining may include medical books, medical treatises, clinical practice guidelines, medical dictionaries, medical corpora, medical knowledge bases, data sets for machine learning (e.g., learning data, training data), data sets for data mining (e.g., big data), or other types of data and/or information.

Note that the knowledge herein includes, for example, information that may be recognized and explicitly expressed, and includes at least either one of empirical knowledge (e.g., knowledge acquired through experience or learning) and theoretical knowledge (e.g., theoretical background knowledge or system of specialized information). Typical examples of the knowledge herein include facts, rules, laws, judgment criteria, common sense, know-how, dictionaries, corpora, and others. In addition, the knowledge herein may include information relating to processing executed by an artificial intelligence processor (also referred to as an artificial intelligence engine or the like). For example, the knowledge herein may include weight parameters and bias parameters used in a neural network.

In machine learning, by (mainly statistically) analyzing the data collected in the way described above, the knowledge acquisition processor 5110 extracts laws, rules, knowledge representations, judgment criteria, and the like from the data analyzed, and further develop an algorithm of inference (described later) based on the information extracted.

The machine learning algorithm applicable to the knowledge acquisition processor 5110 is optional. Examples of the machine learning algorithm include supervised learning, unsupervised learning, semi supervised learning, transduction, and multitasking learning. Furthermore, examples of techniques applicable to the machine learning executed by the knowledge acquisition processor 5110 include decision tree learning, association rule learning, neural network, genetic programming, inductive logic programming, support vector machine, clustering, Bayesian network, reinforcement learning, and feature learning (representation learning).

In data mining, the knowledge acquisition processor 5110 acquires knowledge by applying, to the data as described above, data analysis techniques such as statistics, pattern recognition, artificial intelligence, or other techniques.

Examples of data analysis methods applicable to the data mining executed by the knowledge acquisition processor 5110 include frequent pattern extraction, classification, regression analysis, and clustering.

The knowledge acquisition processor 5110 may be capable of executing any image processing. Examples of the image processing include image enlargement, image reduction, image compression, image decompression, image rotation, binarization, gray scale representation, pseudo-color representation, contrast adjustment, smoothing, histogram, color information extraction, gamma correction, color correction, contour extraction (edge detection), noise removal (noise reduction), size measurement, feature extraction, pattern recognition, rendering, cross section conversion, and characteristic map creation.

In the present embodiment, the knowledge acquisition processor 5110 may execute at least one of the machine learning and the data mining based at least on a plurality of three dimensional images that includes three dimensional images acquired by slit lamp microscopes.

Further, the knowledge acquisition processor 5110 may be configured to execute at least one of the machine learning and the data mining based on a plurality of three dimensional images and a plurality of front images that include three dimensional images and front images acquired by slit lamp microscopes.

Furthermore, the knowledge acquisition processor 5110 may be configured to execute at least one of the machine learning and the data mining based on a plurality of three dimensional images and a plurality of pieces of subject information that include three dimensional images acquired by slit lamp microscopes and subject information input to slit lamp microscopes.

The knowledge acquired by the knowledge acquisition processor 5110 is stored in the knowledge storage 5320 of the storage device 5300. The knowledge storage 5320 may store not only the knowledge acquired by the knowledge acquisition processor 5110 but also the above-described various kinds of knowledge and/or data used in the knowledge acquisition processing.

<Inference Processor 5120>

The inference processor 5120 is configured to perform inference based on the three dimensional image of the subject's eye received by the information processing system 5000 from one of the plurality of the ophthalmic imaging apparatuses 2000-$i_n$ (e.g., the slit lamp microscope 1) and the knowledge stored in the knowledge storage 5320. The inference generates information for supporting diagnosis of the subject. This information is referred to as diagnosis support information. The inference processor 5120 includes, for example, an inference engine (semantic reasoner) configured to derive an answer from a knowledge base.

In the event that the knowledge acquisition processor 5110 is configured to execute machine learning, the inference processor 5120 may execute inference using an inference algorithm developed by the machine learning.

In the event that the knowledge acquisition processor 5110 is configured to execute data mining, the inference processor 5120 may execute inference using knowledge acquired by the data mining.

In the event that the knowledge acquisition processor 5110 is configured to execute both machine learning and data mining, the inference processor 5120 may execute inference using at least one of an inference algorithm developed by the machine learning and knowledge acquired by the data mining.

Examples of inferred items or matters include a suspected disease name, presence or absence of a specific disease, severity, necessity for examination, examination type, necessity for a surgery, surgery type, and other items or matters.

Note that the inference herein means, for example, to derive unknown information from known information. Examples of the inference includes deduction, induction, abduction, complete knowledge based inference or reasoning, incomplete knowledge based inference or reasoning, object knowledge level inference, meta knowledge level inference, and other types. The inference is executed, for example, based on any one or more of medical knowledge, expertise in other fields, general knowledge, and knowledge acquired using an artificial intelligence technique or technology.

<Communication Unit 5200>

The communication unit 5200 is configured to perform data communication with another apparatus (e.g., the ophthalmic imaging apparatus 2000-$i_n$, the computer terminal 3000-$n$, etc.). The system of the data communication, encryption, etc. may be performed in the same manner as in the communication unit 170 of the ophthalmic imaging apparatus 2000-$i_n$.

<Storage Device 5300>

The storage device 5300 is configured to store various kinds of data. The storage device 5300 includes, for example, at least one of a semiconductor storage device, a magnetic storage device, an optical storage device, and a magneto-optical storage device. The storage device 5300 may include two or more storage devices.

The storage device 5300 includes the photographed data storage 5310, the knowledge storage 5320, and the diagnosis support information storage 5330.

The photographed data storage 5310 is configured to store data used in processing executed by the knowledge storage 5320. Examples of data stored in the photographed data storage 5310 include the followings: data acquired by the ophthalmic imaging apparatuses 2000-$i_n$ (e.g., three dimensional images, front images, and cross sectional images); data acquired by other ophthalmic imaging apparatuses (e.g., three dimensional images, front images, and cross sectional images); analysis data of images (e.g., segmentation data, layer thickness data, size data, density data, and shape data); data acquired by ophthalmic examination apparatuses (e.g., visual acuity values, eye refractive power values, corneal curvature values, intraocular pressure values, corneal endothelial cell density values, aberration values of ocular optical systems, and visual field examination data); data acquired by apparatuses used in other medical departments (e.g., X-ray images, X-ray computed tomography (CT) images, magnetic resonance imaging (MRI) images, positron emission tomography (PET) images, single photon emission computed tomography (SPECT) images, and ultrasound images); biological tissue diagnosis data; blood test data; electronic medical record data; interpretation reports; data used for machine learning and/or data mining. Examples of the data used for machine learning and/or data mining include medical knowledge, knowledge in other academic fields, knowledge in any fields other than academic fields, medical books, medical treatises, clinical practice guidelines, medical dictionaries, medical corpora, medical knowledge bases, data sets for machine learning (e.g., learning data, training data), and data sets for data mining (e.g., big data).

The knowledge storage 5320 is configured to store the knowledge acquired by the knowledge acquisition processor 5110. In addition to the knowledge acquired by the knowledge acquisition processor 5110, the followings are some examples of data stored in the knowledge storage 5320: data acquired by the ophthalmic imaging apparatuses $2000\text{-}i_n$ (e.g., three dimensional images, front images, and cross sectional images); data acquired by other ophthalmic imaging apparatuses (e.g., three dimensional images, front images, and cross sectional images); analysis data of images (e.g., segmentation data, layer thickness data, size data, density data, and shape data); data acquired by ophthalmic examination apparatuses (e.g., visual acuity values, eye refractive power values, corneal curvature values, intraocular pressure values, corneal endothelial cell density values, aberration values of ocular optical systems, and visual field examination data); data acquired by apparatuses used in other medical departments (e.g., X-ray images, X-ray computed tomography (CT) images, magnetic resonance imaging (MRI) images, positron emission tomography (PET) images, single photon emission computed tomography (SPECT) images, and ultrasound images); biological tissue diagnosis data; blood test data; electronic medical record data; interpretation reports; data used for machine learning and/or data mining. Examples of the data used for machine learning and/or data mining include medical knowledge, knowledge in other academic fields, knowledge in any fields other than academic fields, medical books, medical treatises, clinical practice guidelines, medical dictionaries, medical corpora, medical knowledge bases, data sets for machine learning (e.g., learning data, training data), and data sets for data mining (e.g., big data). In this manner, the knowledge storage 5320 stores the knowledge bases used by the inference processor 5120.

The diagnosis support information storage 5330 is configured to store the inference result (i.e., diagnosis support information) derived by the inference processor 5120.

<Usage Mode>

Figure 8:
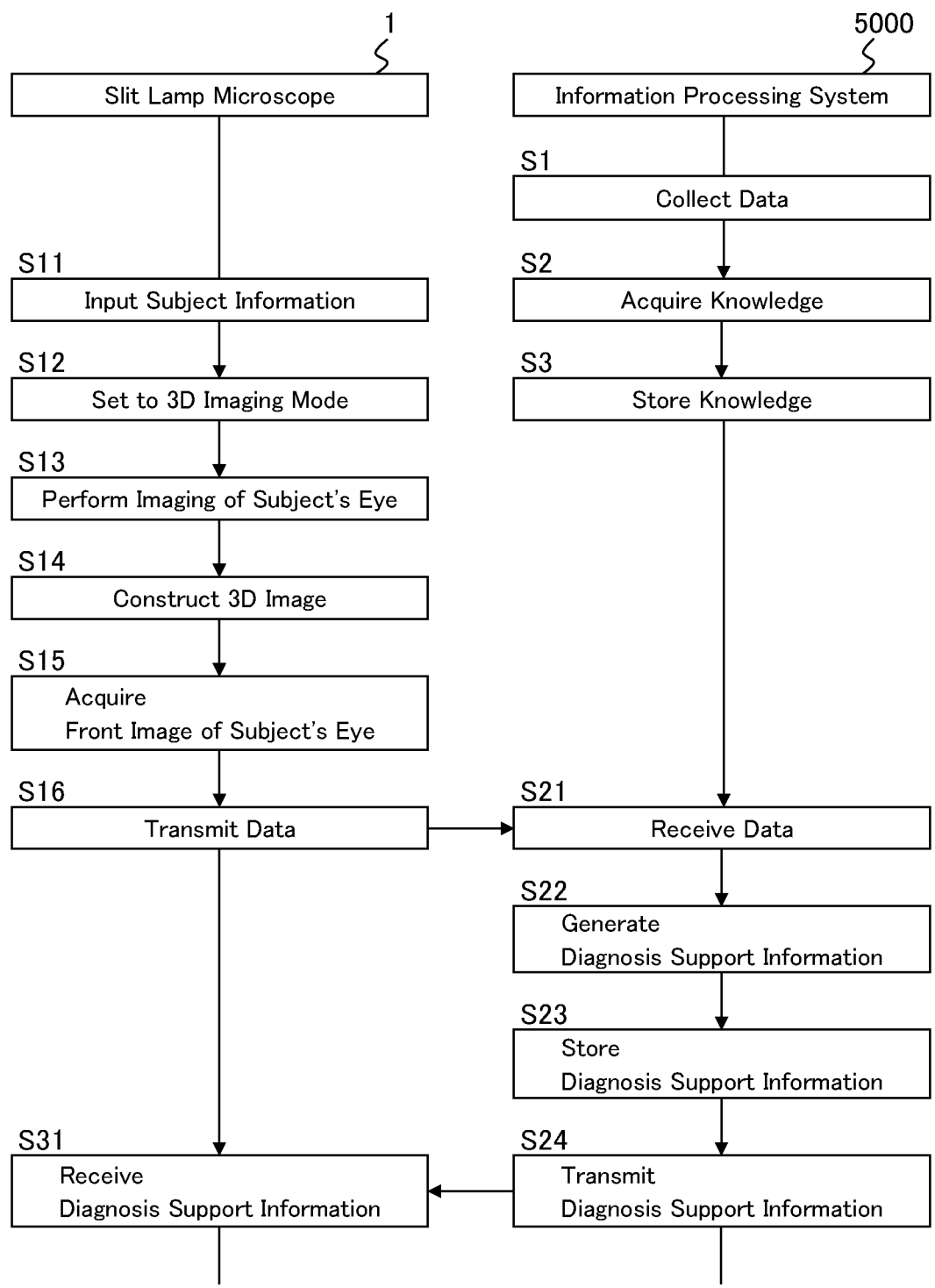
FIG. 8 is a sequence diagram illustrating an example of a usage mode of the ophthalmic system according to the embodiment example.

The usage mode of the ophthalmic system 1000 according to the present embodiment will be described. FIG. 8 shows an example of the usage mode of the ophthalmic system 1000.

It is assumed that communication between the ophthalmic imaging apparatuses $2000\text{-}i_n$ such as the slit lamp microscope 1 (and/or the computer terminals 3000-n) and the information processing system 5000 has already been established. Alternatively, communication between the ophthalmic imaging apparatus $2000\text{-}i_n$ such as the slit lamp microscope 1 (and/or the computer terminal 3000-n) and the information processing system 5000 may be established at any timing before or at the step S16 in FIG. 8.

(S1: Collect Data)

First, the information processing system 5000 collects various kinds of data for acquiring knowledge to be used in the generation of diagnosis support information from an three dimensional image of an subject's eye acquired by a slit lamp microscope.

The input of data to the information processing system 5000 is carried out via at least one of a communication path such as the communication path N, an information recording medium, and a data reader such as a scanner, for example. Data may be manually input to the information processing system 5000. The data input to the information processing system 5000 is stored in the photographed data storage 5310 by the controller 5010.

The data collected in the step S1 includes at least a plurality of three dimensional images acquired by slit lamp microscopes. Further, the data collected in the step S1 may include any of the followings: images acquired by ophthalmic imaging apparatuses (e.g., the ophthalmic imaging apparatuses $2000\text{-}i_n$ or other ophthalmic imaging apparatuses) other than a slit lamp microscope, and/or data obtained by processing or analyzing such images; examination data obtained by ophthalmic examination apparatuses, and/or data obtained by processing or analyzing such examination data; data acquired by apparatuses used in other medical departments, and/or data obtained by processing or analyzing such data; data included in the information input by doctors (e.g., electronic medical records, interpretation reports), and/or data obtained by processing or analyzing such data; medical knowledge, knowledge in other academic fields, knowledge in any fields other than academic fields; and information and/or data used to obtain the knowledge listed above. Note that examples of the data enumerated here have already been described.

(S2: Acquire Knowledge)

The knowledge acquisition processor 5110 executes at least one of machine learning and data mining based on at least part of the data collected in the step S1 and stored in the photographed data storage 5310. Here, the data used for the machine learning and/or data mining includes at least a plurality of three dimensional images acquired by slit lamp microscopes. The machine learning and/or data mining acquires knowledge based on the concerned data.

(S3: Store Knowledge)

The controller 5010 stores the knowledge acquired in the step S2 in the knowledge storage 5320.

Note that the processes of the steps S1 to S3 may be repeated. For example, when new data has been input to the information processing system 5000, the ophthalmic system 1000 may execute processing for acquiring new knowledge. Such processing is performed at predetermined time intervals, for example. Alternatively, such processing may be repeated according to the amount of new data accumulated. As another example, knowledge may be acquired based on each of the first to K-th partial data of the data stored in the photographed data storage 5310. Each piece of knowledge acquired by such repeated processing is stored in the knowledge storage 5320 by the controller 5010.

(S11: Input Subject Information)

Subject information is input to the slit lamp microscope 1 (or to the computer terminal 3000-*n*) included in the ophthalmic system 1000. The subject information is stored in the memory 102. If communication between the slit lamp microscope 1 (and/or the computer terminal 3000-*n*) and the information processing system 5000 has already been established, the subject information may be transmitted to the information processing system 5000 at this stage. The subject information includes, for example, a subject identifier (subject ID) and background information.

The subject ID includes, for example, an identifier in a medical facility (e.g., a patient ID), an identifier for a medical check, an identifier for a medical examination, or the like. These are examples only, and the kinds of the subject IDs are not limited to them.

The background information is any kind of information related to the subject, and includes, for example, information recorded for an arbitrary item or matter in the electronic medical record of the subject, an image stored in the subject's account, and the like. Typically, the background information includes the subject's data on items such as sex, age, height, weight, contracted disease name, possible disease name, examination results (e.g., visual acuity values, eye refractive power values, intraocular pressure values, etc.), images (e.g., OCT images, fundus images, anterior eye segment images, etc.), examination history, and treatment history. These are examples only, and the items in the background information are not limited to them. In a typical example, the background information includes data corresponding to data items to which the information processing system 5000 has referred for the knowledge acquisition.

The user of the slit lamp microscope 1 (or the user of the computer terminal 3000-*n*) may input subject information using the operation device 140, for example. In addition, the controller 101 and the communication unit 170 may access an information system such as an electronic medical record system or a medical image archiving system via a communication path, to acquire subject information. In another example, subject information may be read out from a recording medium using a data reader. These are examples only, and the methods of inputting subject information are not limited to them.

(S12: Set to Three Dimensional Imaging Mode)

The operation mode of the slit lamp microscope 1 is set to the three dimensional imaging mode. As described above, the designation (or selection) of the operation mode is conducted manually or automatically.

(S13: Perform Imaging of Subject's Eye)

The slit lamp microscope 1 conducts the imaging of the subject's eye E with the three dimensional imaging mode that has been set in the step S12. With this, a plurality of cross sectional images of the subject's eye E is acquired.

(S14: Construct Three Dimensional Image)

The image composer 120 of the slit lamp microscope 1 constructs a three dimensional image, based on the plurality of cross sectional images acquired in the step S13. Note that the information processing system 5000 or another apparatus may perform the three dimensional image construction.

(S15: Acquire Front Image of Subject's Eye)

The slit lamp microscope 1 may acquire a front image of the subject's eye E. The execution stage of the front image acquisition is not limited to this stage. Note that the front image acquisition is optional in the present usage mode.

(S16: Transmit Data)

The controller 101 of the slit lamp microscope 1 controls the communication unit 170 to transmit the acquired data to the information processing system 5000. The transmitted data includes at least the three dimensional image constructed in the step S14 and may further include any one or both of the subject information input in the step S11 and the front image acquired in the step S15.

If an apparatus other than the slit lamp microscope 1 executes three dimensional image construction, the plurality of cross sectional images acquired in the step S13 is transmitted to the apparatus, and a three dimensional image constructed by the apparatus is referred to by the information processing system 5000.

(S21: Receive Data)

The communication unit 5200 of the information processing system 5000 receives the data transmitted from the slit lamp microscope 1 in the step S16. The controller 5010 stores the received data in the storage device 5300.

Note that at least part of the data received in the step S21 may be stored in the photographed data storage 5310 and used for new knowledge acquisition processing.

(S22: Generate Diagnosis Support Information)

The inference processor 5120 performs inference based on at least part of the data on the subject's eye E (and the data of the subject) received in the step S21 and at least part of the knowledge stored in the knowledge storage 5320. With this, diagnosis support information regarding the subject's eye E is generated.

The diagnosis support information may include, for example, any of a suspected disease name, presence or absence of a specific disease, severity, necessity for an examination, a type of examination, necessity for a surgery, a type of surgery, and other information.

(S23: Store Diagnosis Support Information)

The controller 5010 stores the diagnosis support information generated in the step S22 into the diagnosis support information storage 5330.

Note that at least part of the diagnosis support information generated in the step S22 may be stored in the photographed data storage 5310 and used for new knowledge acquisition processing.

(S24: Transmit Diagnosis Support Information)

Further, the controller 5010 controls the communication unit 5200 to transmit the diagnosis support information generated in the step S22 to the slit lamp microscope 1 (and/or, to the computer terminal 3000-*n* and/or another apparatus). Here, examples of another apparatus include the followings: a computer used by the doctor in charge of the subject; a server installed in the health facility where the subject is receiving medical consultation; and a computer installed outside this health facility (e.g., a computer installed in a core hospital, a specialized health facility, a medical data analysis facility or institution, etc.).

For example, when transmitting the diagnosis support information to a computer installed outside the health facility where the subject is receiving medical consultation, the following information may be transmitted along with the diagnosis support information: at least part of the data on the subject's eye E (and the data of the subject) received in the step S21; and at least part of the knowledge and/or data referred to in the step S22.

(S31: Receive Diagnosis Support Information)

The slit lamp microscope 1 (and another apparatus) receives the diagnosis support information transmitted from the information processing system 5000 in the step S24. The doctor in charge of the subject may make a diagnosis with reference to the diagnosis support information received. In addition, the diagnosis support information may be automatically entered in the electronic medical record and/or interpretation report of the subject's. This is the end of the processes according to the present example.

MODIFICATION EXAMPLES

Some modification examples of the present embodiment will be described.

The configuration for changing the focal positions of the slit lamp microscope 1 is not limited to the focus mechanisms 40 and 50 described above.

For example, it is possible to employ a slit lamp microscope that is configured to acquire two or more images of a subject's eye using two or more photographing devices (two or more anterior segment cameras), disclosed in Japanese Unexamined Patent Application Publication No. 2013-248376, and then determine the focal positions (target positions) by analyzing the images acquired by the two or more photographing devices.

Another example of the configuration for changing the focal positions is the following. A slit lamp microscope of the present example includes an imaging device, a driver, and a focus controller. The imaging device is configured to photograph a subject's eye to acquire a right image and a left image. The driver is configured to move an optical system of the slit lamp microscope, which includes the imaging device, at least in the direction along the working distance. The focus controller is configured to control the driver, based on the right image and the left image acquired by the imaging device, to automatically perform the focusing operation on the subject's eye.

Second Embodiment: Ophthalmic System

The ophthalmic system according to the present embodiment has substantially the same configuration as that of the first embodiment. Hereinafter, differences from the first embodiment will be mainly described. Elements same as or similar to those in the first embodiment are indicated by the same reference characters. The elements indicated by the same reference characters as those in the first embodiment have the same or like configuration and the same or like functions as those in the first embodiment, unless otherwise specified.

Figure 9:
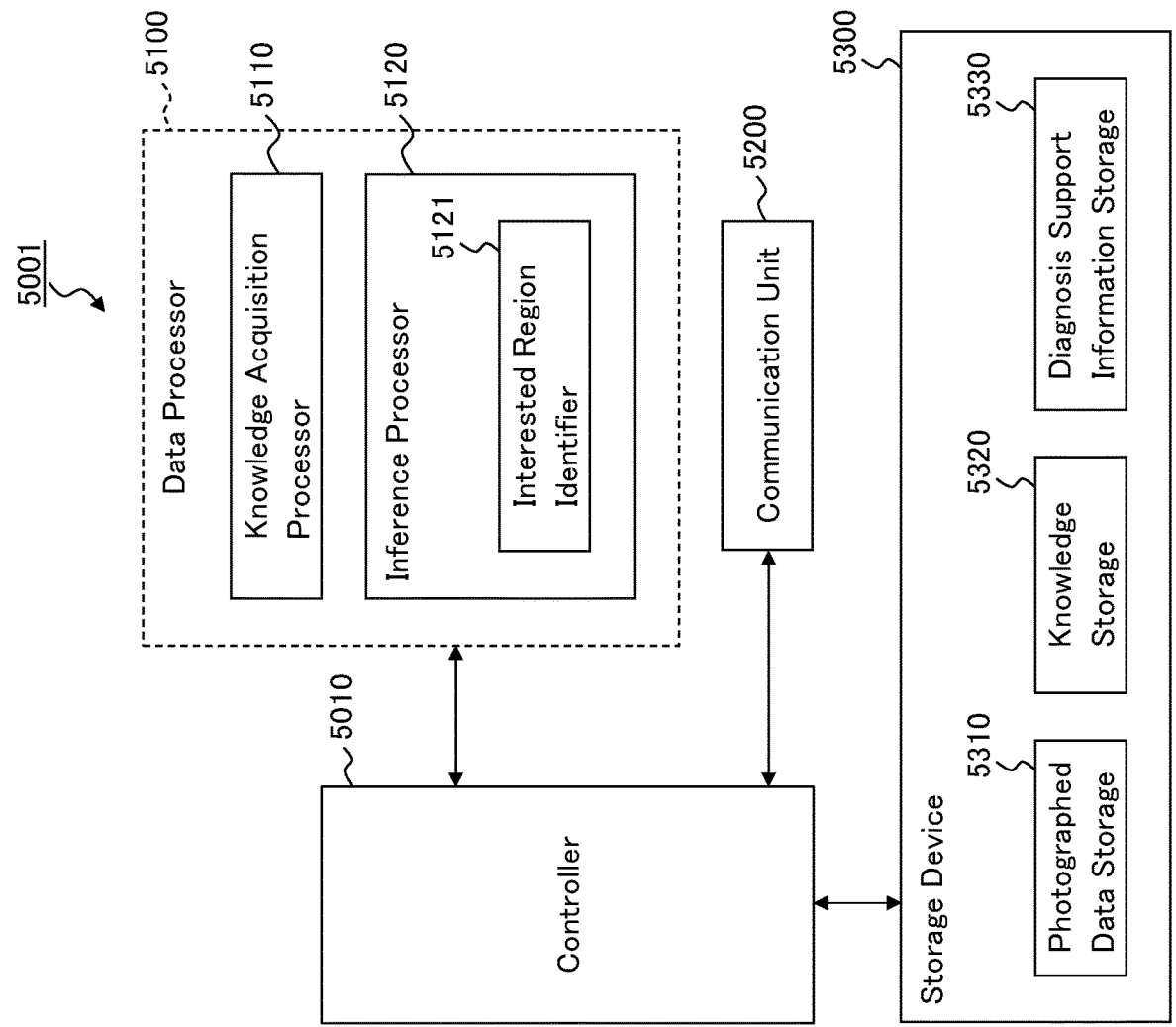
FIG. 9 is a schematic diagram illustrating an example of the configuration of the ophthalmic system according to the embodiment example.

FIG. 9 shows a configuration example of the information processing system included in the ophthalmic system according to the present embodiment. The information processing system 5001 is provided in place of or in addition to the information processing system 5000 of the first embodiment shown in FIG. 1.

The information processing system 5001 is different from the information processing system 5000 of the first embodiment in that the inference processor 5120 includes the interested region identifier 5121.

The interested region identifier 5121 is configured to identify an interested region by analyzing a three dimensional image of the subject's eye E acquired by the slit lamp microscope 1 and input to the information processing system 5001. The interested region is subjected to inference processing executed by the inference processor 5120, for example. Therefore, the inference processor 5120 of the present embodiment may generate diagnosis support information about the subject's eye E by conducting inference based on the interested region identified from the three dimensional image by the interested region identifier 5121 and the knowledge stored in the knowledge storage 5320.

In comparison to the case of processing the entire three dimensional image, setting the interested region brings benefits such as saving of the computational resources, simplifying of the inference algorithm, and shortening of the processing time.

The interested region identifying processing is executed, for example, by a method similar to the conventional method. For example, the interested region identifier 5121 applies segmentation to a three dimensional image to identify an image region corresponding to a specific site of the subject's eye E. Examples of the specific site include a specific layer(s) of the cornea, the iris, the pupil, the corner angle, the crystalline lens, the ciliary muscle, the Zinn's zonule, the optic nerve head, the macular, the blood vessel(s). Further, the interested region identifier 5121 may identify a feature site (e.g., an abnormal site etc.) by analyzing the size, thickness, shape, etc. of a partial region of the three dimensional image. The interested region identification may employ any kinds of image processing such as edge detection, size measurement, feature extraction, pattern recognition, rendering, and cross section conversion.

Furthermore, the interested region identification may also employ any kinds of artificial intelligence techniques or technologies. In that case, at least part of the knowledge stored in the knowledge storage 5320 may be used.

Third Embodiment: Ophthalmic System

The ophthalmic system according to the present embodiment has substantially the same configuration as that of the first embodiment. Hereinafter, differences from the first embodiment will be mainly described. Elements same as or similar to those in the first embodiment are indicated by the same reference characters. The elements indicated by the same reference characters as those in the first embodiment have the same or like configuration and the same or like functions as those in the first embodiment, unless otherwise specified.

Figure 10:
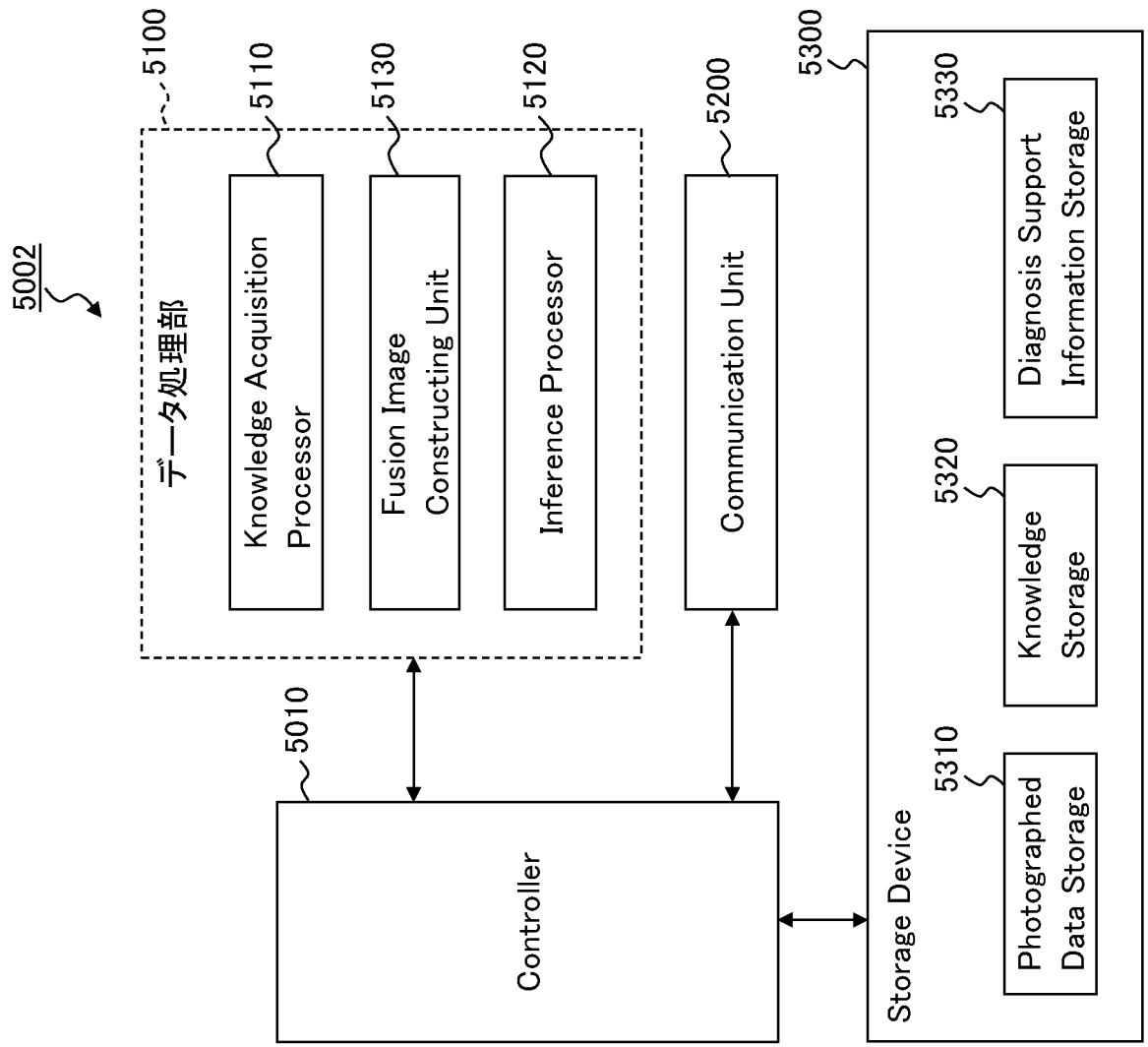
FIG. 10 is a schematic diagram illustrating an example of the configuration of the ophthalmic system according to the embodiment example.

FIG. 10 shows a configuration example of the information processing system included in the ophthalmic system according to the present embodiment. The information processing system 5002 is provided in place of or in addition to the information processing system 5000 of the first embodiment shown in FIG. 1.

The information processing system 5002 is different from the information processing system 5000 of the first embodiment in that the data processor 5100 includes the fusion image constructing unit 5130.

While the information processing system 5002 has the function of constructing fusion images in the present embodiment, other apparatuses may have the fusion image constructing function in other embodiments. For example, the fusion image constructing function may be provided in any one or more of the ophthalmic imaging apparatuses 2000-$i_n$ (i.e., the slit lamp microscopes 1 or other modality apparatuses), the computer terminals 3000-$n$, and other apparatuses.

In the present embodiment, the plurality of the ophthalmic imaging apparatuses 2000-$i_n$ includes one or more of the slit lamp microscopes 1 and one or more modality apparatuses of a different type(s) from slit lamp microscopes. Other modality apparatuses may be, for example, ophthalmic imaging apparatuses or ophthalmic examination apparatuses. Examples of the ophthalmic imaging apparatuses include OCT apparatuses, fundus cameras, SLOs, and surgical microscopes. Examples of the ophthalmic examination apparatuses include specular microscopes, wave front analyzers, microperimeters, and corneal topographers.

The fusion image constructing unit 5130 is configured to compose a three dimensional image of the subject's eye E acquired by the slit lamp microscope 1 and an image(s) acquired by one or more other modality apparatuses, to construct a fusion image.

An image acquired by the one or more other modality apparatuses is, for example, a two dimensional image or a three dimensional image. The image may be an image representing morphology (structure) and/or a function of the subject's eye E, or may be a characteristic map of the subject's eye E.

Examples of an image representing morphology of the subject's eye E (referred to as a morphological image) include the followings: an OCT morphological image (e.g., a three dimensional image, a rendered image of a three dimensional image, a two dimensional cross sectional image, a blood vessel emphasized image (angiogram), etc.); an anterior eye segment image; and a fundus photograph (e.g., a color image, a monochrome image, a red free image, a single color image, etc.).

Examples of an image representing a function of the subject's eye E include the followings: an OCT functional image (e.g., a phase image, a blood flow image, a polarization image, etc.); and a fundus photograph (e.g., a fluorescein fluorescence image, an indocyanine green fluorescence image, an autofluorescence image, etc.).

Examples of a characteristic map of the subject's eye E include a corneal layer thickness map, a corneal topograph, a corneal endothelial cell density map, an aberration map, a visual field map (sensitivity map), a retinal layer thickness map, a choroid layer thickness map, and the like.

Other modality apparatuses may not be ophthalmic modalities. For example, an image of the subject's eye E (or its peripheral part) acquired by MRI, ultrasonography, PET, SPECT, or the like may be used for fusion image construction.

A fusion image is an image obtained by composing two or more images of the same subject's eye E. The two or more images to be composed may be images acquired by the same modality or may include images acquired by two or more different modalities. Note that an image obtained by panoramic composition of two or more images acquired by conducting imaging (photographing) of two or more different regions of the subject's eye E is supposed to be a kind of fusion images obtained by composing two or more images acquired by the same modality.

In the present embodiment, the photographed data storage 5310 may store any one or more of the following kinds of data: an image acquired by a modality other than slit lamp microscope; data obtained by processing or analyzing an image acquired by a modality other than slit lamp microscope; a fusion image; and data obtained by processing or analyzing a fusion image.

Likewise, the knowledge storage 5320 may store any one or more of the following kinds of data: knowledge acquired from an image acquired by a modality other than slit lamp microscope; knowledge acquired from data obtained by processing or analyzing an image acquired by a modality other than slit lamp microscope; knowledge acquired from a fusion image; and knowledge acquired from data obtained by processing or analyzing a fusion image.

Some examples of processing executed by the fusion image constructing unit 5130 will be described. To begin with, the fusion image constructing unit 5130 executes one or more of the followings: extraction of one or more partial images, to be composed, from a three dimensional image of the subject's eye E acquired by the slit lamp microscope 1; and extraction of one or more partial images, to be composed, from an image acquired by another modality apparatus. Note that this process is optional.

Next, the fusion image constructing unit 5130 performs position matching (registration) between the three dimensional image of the subject's eye E acquired by the slit lamp microscope 1 and the image acquired by another modality apparatus. As in the conventional case, the registration includes the following processes, for example: a process of detecting one or more feature points and/or one or more feature regions from each of the two or more images to be composed; and a process of adjusting the relative position of the two or more images on the basis of the one or more feature points and/or the one or more feature regions detected.

It should be noted that the partial image extraction may be performed after the registration.

Further, the fusion image constructing unit 5130 composes the registered three dimensional image (or the registered one or more partial images of the three dimensional image) acquired by the slit lamp microscope 1 and the registered image (or the registered one or more partial images of the image) acquired by another modality apparatus, thereby constructing a fusion image. Here, the fusion image constructing unit 5130 may be configured to apply any image processing to images yet to be composed and/or to a resulting fusion image. Examples of applicable image processing herein include alpha blending, brightness correction, color correction, contrast adjustment, image enlargement, image reduction, image compression, image decompression, image rotation, pseudo-color representation, smoothing, and gamma correction.

The inference processor 5120 may perform inference for generation of diagnosis support information relating to the subject's eye E, based on the fusion image constructed by the fusion image constructing unit 5130 (and, one or more of the images before composition, the front image, the subject information, and other data) and on the knowledge stored in the knowledge storage 5320.

Fourth Embodiment: Ophthalmic Information Processing Device

The ophthalmic information processing device according to the present embodiment may have the same configuration as the information processing system 5000 of the first embodiment (or, as the information processing system 5001 or 5002 of the second or third embodiment). More specifically, the ophthalmic information processing device of the present embodiment has both the knowledge acquisition function and the inference function. The configuration and functions of the ophthalmic information processing device of the present embodiment are the same as those of any of the information processing systems in the first to third embodiments. Consequently, the descriptions of the configuration and functions of the ophthalmic information processing device of the present embodiment are omitted.

Fifth Embodiment: Ophthalmic Information Processing Device

The ophthalmic information processing device according to the present embodiment has the inference function but does not have the knowledge acquisition function. In the present embodiment, the knowledge acquisition processing is performed by another apparatus or device having a knowledge acquisition function the same as or similar to the knowledge acquisition function of the information processing system 5000 of the first embodiment, for example. The ophthalmic information processing device of the present embodiment receives and stores knowledge acquired by another apparatus or device.

Figure 11:
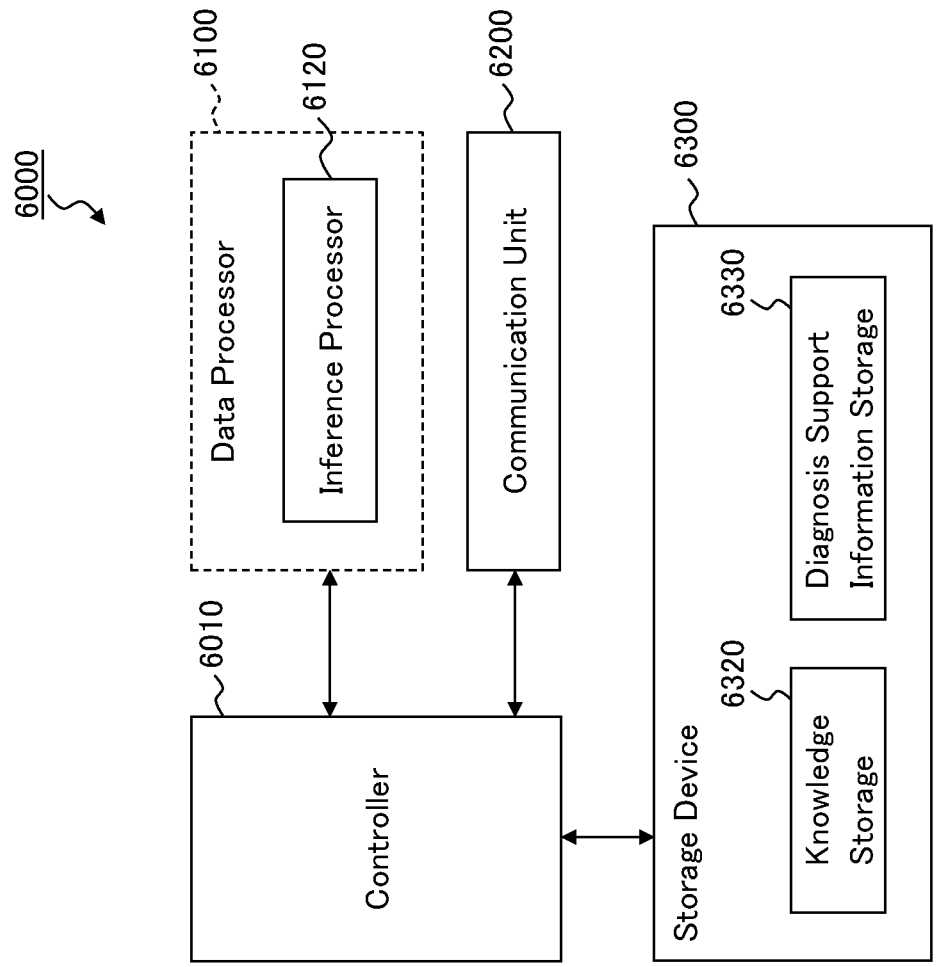
FIG. 11 is a schematic diagram illustrating an example of the configuration of the ophthalmic information processing device according to the embodiment example.

FIG. 11 shows an example of the configuration of the ophthalmic information processing device according to the present embodiment. The ophthalmic information processing device 6000 includes the controller 6010, the data processor 6100, the communication unit 6200, and the storage device 6300. The data processor 6100 includes the inference processor 6120. Unlike the data processor 5100 of the first embodiment etc., the data processor 6100 may not include the knowledge acquisition processor 5110. The storage device 6300 includes the knowledge storage 6320 and the diagnosis support information storage 6330.

The controller 6010 has the same or similar configuration and the same or similar functions as or to those of the controller 5010 in the first embodiment, for example.

The knowledge storage 6320 stores knowledge acquired by performing at least one of machine learning and data mining based on a plurality of three dimensional images acquired by a plurality of ophthalmic imaging apparatuses including at least a plurality of slit lamp microscopes. The knowledge storage 6320 has the same or similar configuration and the same or similar functions as or to those of the knowledge storage 5320 in the first embodiment, for example.

The communication unit 6200 is configured to receive a three dimensional image of the subject's eye acquired by a slit lamp microscope via a communication path. The communication unit 6200 has, for example, the same or similar configuration and the same or similar functions as or to those of the communication unit 5200 in the first embodiment.

The inference processor 6120 is configured to conduct inference based on the three dimensional image received by the communication unit 6200 and the knowledge stored in the knowledge storage 6320, and generates diagnosis support information for the subject's eye. The inference processor 6120 has the same or similar configuration and the same or similar functions as or to those of the inference processor 5120 in the first embodiment, for example.

The diagnosis support information generated by the inference processor 6120 is stored in the diagnosis support information storage 6330 by the controller 6010. The diagnosis support information storage 6330 has the same or similar configuration and the same or similar functions as or to those of the diagnosis support information storage 5330 in the first embodiment, for example.

<Actions and Effects>

Some actions and some effects of the embodiments described above will be described.

The ophthalmic system (1000) according to some embodiments includes a plurality of ophthalmic imaging apparatuses (2000-$i_n$) and image processing system (5000, 5001, 5002). The image processing system is connected to each of the plurality of ophthalmic imaging apparatuses via one or more communication paths (N). The plurality of ophthalmic imaging apparatuses includes a plurality of slit lamp microscopes (1).

Each of the plurality of ophthalmic imaging apparatuses includes an image acquisition unit (the observation-photographing system 6, the illumination system 8, the movement mechanism 60, etc.) and a first communication unit (the communication unit 170).

The image acquisition unit is configured to acquire a three dimensional image by photographing a subject's eye.

The first communication unit is configured to transmit the three dimensional image acquired by the image acquisition unit to the information processing system.

Here, the configuration of "transmitting to the information processing system" includes at least one of a configuration of transmitting directly to the information processing system and a configuration of transmitting indirectly to the information processing system via another apparatus.

The information processing system includes a second communication unit (5200), an image storage (the photographed data storage 5310), a first processor (the knowledge acquisition processor 5110), a knowledge storage (5320), and a second processor (the inference processor 5120).

The second communication unit is configured to receive the three dimensional image transmitted by the first communication unit of the ophthalmic imaging apparatus.

The image storage is configured to store a plurality of three dimensional images received by the second communication unit.

The first processor is configured to perform at least one of machine learning and data mining, based on the plurality of three dimensional images stored in the image storage. With this, knowledge is acquired.

The knowledge storage is configured to store the knowledge acquired by the first processor.

The second processor is configured to generate diagnosis support information for the subject's eye by conducting inference based on a three dimensional image of a subject's eye transmitted from one of the plurality of slit lamp microscopes and received by the second communication unit and based on knowledge stored in the knowledge storage.

The ophthalmic system of some embodiments configured as described above is capable of acquiring a three dimensional image of a subject's eye using a slit lamp microscope, which is most widely and frequently used in ophthalmic diagnostic imaging, and sending the three dimensional image to the information processing system. In addition, the ophthalmic system is capable of generating diagnosis support information from the three dimensional image by inference using knowledge acquired in advance by at least one of machine learning and data mining.

Therefore, according to the ophthalmic system of some embodiments, analysis by artificial intelligence of an image acquired using a slit lamp microscope, which has been difficult with the conventional techniques and technologies, may be suitably carried out.

In some embodiments, the second processor (the inference processor 5120) may include an interested region identifier (the interested region identifier 5121) configured to identify an interested region of the three dimensional image of the subject's eye by analyzing the three dimensional image of the subject's eye acquired by a slit lamp microscope.

Furthermore, the second processor (the inference processor 5120) of some embodiments may be configured to generate diagnosis support information by performing inference based on the interested region identified by the interested region identifier and based on knowledge stored in the knowledge storage.

Such a configuration serves to save computational resources, simplify an inference algorithm, and shorten processing time, in comparison to the case of processing the entire three dimensional image.

In some embodiments, the plurality of ophthalmic imaging apparatuses may include one or more modality apparatuses of types different from a slit lamp microscope. In addition, the ophthalmic system of some embodiments may include a fusion image constructing unit (5130). The fusion image constructing unit is configured to construct a fusion image by composing a three dimensional image acquired by one of the plurality of slit lamp microscopes and an image acquired by one of the one or more modality apparatuses. Further, the second processor (the inference processor 5120) may be configured to generate diagnosis support information by performing inference based on the fusion image constructed by the fusion image constructing unit and knowledge stored in the knowledge storage.

In a typical example, the one or more modality apparatuses may include one or more optical coherence tomography (OCT) apparatuses. In this case, the fusion image constructing unit may be configured to construct a fusion image by composing a three dimensional image acquired by one of the plurality of slit lamp microscopes and an image acquired by one of the one or more OCT apparatuses.

According to such a configuration, images obtained with different modalities may be processed in an integrated manner. For example, in the event of visible photographing of a subject's eye having opacity in the optic media (e.g., a crystalline lens etc.) using a slit lamp microscope, at least part of the resulting three dimensional image is not depicted in detail due to the opacity. On the other hand, by conducting infrared imaging (e.g., OCT) of a subject's eye having opacity, an image with less influence of opacity is obtained. Composing these images leads to the improvement of the accuracy and precision of inference.

In addition, if a characteristic map or the like and a three dimensional image acquired by a slit lamp microscope are composed, inference may be made in consideration of the distribution of characteristics of the subject's eye.

In some embodiments, the image acquisition unit of the ophthalmic imaging apparatus (e.g., a slit lamp microscope) may be configured to further acquire a front image by photographing the subject's eye. If this is the case, the first communication unit may be configured to transmit the front image together with the three dimensional image of the eye. The second communication unit of the information processing system may be configured to receive the three dimensional image and the front image transmitted by the first communication unit. The image storage may be configured to store a plurality of three dimensional images and a plurality of front images received by the second communication unit. The first processor may be configured to conduct at least one of machine learning and data mining, based on the plurality of three dimensional images and the plurality of front images stored in the image storage. The knowledge storage may be configured to store knowledge based on the plurality of three dimensional images and the plurality of front images, acquired by the first processor. The second processor may be configured to generate diagnosis support information by conducting inference based on a three dimensional image and a front image of a subject's eye transmitted from one of the plurality of slit lamp microscopes and received by the second communication unit and based on knowledge stored in the knowledge storage.

According to such a configuration, the information processing system may perform the knowledge acquisition processing and the inference processing by further referring to a front image of an eye in addition to a three dimensional image of the eye. This makes it possible to achieve more suitable knowledge acquisition and to perform more suitable inference as compared with the case where the front image is not referred to.

In some embodiments, each of the plurality of ophthalmic imaging apparatuses may further include a receiving unit configured to receive subject information. The receiving unit corresponds to, for example, the operation device 140 and/or the communication unit 170 of the slit lamp microscope 1. The first communication unit may be configured to transmit the subject information together with the three dimensional image of the eye. The second communication unit of the information processing system may be configured to receive the three dimensional image and the subject information transmitted by the first communication unit. The image storage may be configured to store a plurality of three dimensional images and a plurality of pieces of subject information received by the second communication unit. The first processor may be configured to perform at least one of machine learning and data mining, based on the plurality of three dimensional images and the plurality of pieces of subject information stored in the image storage. The knowledge storage may be configured to store knowledge based on the plurality of three dimensional images and the plurality of pieces of subject information, acquired by the first processor. The second processor may be configured to generate diagnosis support information by performing inference based on a three dimensional image of a subject's eye and subject information transmitted from one of the plurality of slit lamp microscopes and received by the second communication unit and based on knowledge stored in the knowledge storage.

According to a configuration as described above, the information processing system is capable of performing the knowledge acquisition processing and the inference processing by further referring to subject information of an eye in addition to a three dimensional image of the eye. This makes it possible to achieve more suitable knowledge acquisition and to perform more suitable inference as compared with the case where subject information is not referred to.

The ophthalmic information processing device (the information processing system 5000) according to some embodiments includes a communication unit (5200), an image storage (the photographed data storage 5310), a first processor (the knowledge acquisition processor 5110), a knowledge storage (5320), and a second processor (the inference processor 5120). The communication unit is configured to receive a plurality of three dimensional images of eyes of subjects acquired by a plurality of ophthalmic imaging apparatuses via a communication path. Here, the plurality of ophthalmic imaging apparatuses includes a plurality of slit lamp microscopes. The image storage is configured to store the plurality of three dimensional images received by the communication unit. The first processor is configured to perform at least one of machine learning and data mining, based on the plurality of three dimensional images stored in the image storage. The knowledge storage is configured to store knowledge acquired by the first processor. The second processor is configured to generate diagnosis support information by performing inference based on a three dimensional image of a subject's eye transmitted from one of the plurality of slit lamp microscopes and received by the communication unit and based on knowledge stored in the knowledge storage.

The ophthalmic information processing device (6000) according to some other embodiments includes a knowledge storage (6320), a communication unit (6200), and a processor (the inference processor 6120). The knowledge storage is configured to store knowledge acquired by performing at least one of machine learning and data mining based on a plurality of three dimensional images acquired by a plurality of ophthalmic imaging apparatuses. Here, the plurality of ophthalmic imaging apparatuses includes a plurality of slit lamp microscopes. The communication unit is configured to receive a three dimensional image of a subject's eye acquired by a slit lamp microscope via a communication path. The processor is configured to generate diagnosis support information by performing inference based on a three dimensional image received by the communication unit and knowledge stored in the knowledge storage.

According to the ophthalmic information processing devices of some embodiments configured as described above, as in the case with the ophthalmic systems of some embodiments, analysis by artificial intelligence of an image acquired with a slit lamp microscope, which has been difficult with the conventional techniques and technologies, may be suitably conducted.

The configurations, embodiments and aspects described above are only typical examples of the present invention. Therefore, any modifications (e.g., omissions, replacements, substitutions, additions, etc.) within the scope of the gist of the present invention may be made as appropriate.

The invention claimed is:

1. An ophthalmic system comprising:
a plurality of ophthalmic imaging apparatuses including a plurality of slit lamp microscopes; and
an information processing system connected to each of the plurality of ophthalmic imaging apparatuses via a communication path, wherein
each of the plurality of slit lamp microscopes includes
a first processor,
an illumination system configured to project slit light onto a subject's eye from a first direction,
an image acquisition unit including a photographing system having a sensor configured to perform photography of the subject's eye in a second direction different from the first direction to acquire a three dimensional image,
a movement mechanism configured to move the illumination system and the photographing system under control of the first processor, and
a first communication circuit configured to transmit the three dimensional image to the information processing system, and
the information processing system includes
a second communication circuit configured to receive the three dimensional image transmitted by the first communication circuit,
an image memory configured to store a plurality of three dimensional images received by the second communication circuit,
a second processor configured to perform at least one of machine learning and data mining, based on the plurality of three dimensional images,
a knowledge memory configured to store knowledge acquired by the second processor, and
a third processor configured to generate diagnosis support information by performing inference based on a three dimensional image of a subject's eye transmitted from one of the plurality of slit lamp microscopes and received by the second communication circuit and based on the knowledge stored in the knowledge memory.

2. The ophthalmic system of claim 1, wherein the third processor includes an interested region identifier configured to identify an interested region of the three dimensional image of the subject's eye by analyzing the three dimensional image.

3. The ophthalmic system of claim 2, wherein the third processor is configured to generate diagnosis support information by performing inference based on the interested region and the knowledge stored in the knowledge memory.

4. The ophthalmic system of claim 1, wherein
the plurality of ophthalmic imaging apparatuses includes one or more of modality apparatuses of one or more types different from a slit lamp microscope,
the ophthalmic system further comprises a fusion image constructing circuit configured to construct a fusion image by composing a three dimensional image acquired by one of the plurality of slit lamp microscopes and an image acquired by one of the one or more modality apparatuses, and
the third processor is configured to generate diagnosis support information by performing inference based on the fusion image and the knowledge stored in the knowledge memory.

5. The ophthalmic system of claim 2, wherein
the plurality of ophthalmic imaging apparatuses includes one or more of modality apparatuses of one or more types different from a slit lamp microscope,
the ophthalmic system further comprises a fusion image constructing circuit configured to construct a fusion image by composing a three dimensional image acquired by one of the plurality of slit lamp microscopes and an image acquired by one of the one or more modality apparatuses, and
the third processor is configured to generate diagnosis support information by performing inference based on the fusion image and the knowledge stored in the knowledge memory.

6. The ophthalmic system of claim 3, wherein
the plurality of ophthalmic imaging apparatuses includes one or more of modality apparatuses of one or more types different from a slit lamp microscope,
the ophthalmic system further comprises a fusion image constructing circuit configured to construct a fusion image by composing a three dimensional image acquired by one of the plurality of slit lamp microscopes and an image acquired by one of the one or more modality apparatuses, and
the third processor is configured to generate diagnosis support information by performing inference based on the fusion image and the knowledge stored in the knowledge memory.

7. The ophthalmic system of claim 4, wherein
the one or more modality apparatuses include one or more optical coherence tomography (OCT) apparatuses, and
the fusion image constructing circuit is configured to construct a fusion image by composing a three dimensional image acquired by one of the plurality of slit lamp microscopes and an image acquired by one of the one or more OCT apparatuses.

8. The ophthalmic system of claim 5, wherein
the one or more modality apparatuses include one or more optical coherence tomography (OCT) apparatuses, and
the fusion image constructing circuit is configured to construct a fusion image by composing a three dimensional image acquired by one of the plurality of slit lamp microscopes and an image acquired by one of the one or more OCT apparatuses.

9. The ophthalmic system of claim 6, wherein
the one or more modality apparatuses include one or more optical coherence tomography (OCT) apparatuses, and
the fusion image constructing circuit is configured to construct a fusion image by composing a three dimensional image acquired by one of the plurality of slit lamp microscopes and an image acquired by one of the one or more OCT apparatuses.

10. The ophthalmic system of claim 1, wherein
the image acquisition unit is configured to further acquire a front image by photographing the subject's eye,
the first communication circuit is configured to transmit the front image together with the three dimensional image,
the second communication circuit is configured to receive the three dimensional image and the front image transmitted by the first communication circuit,
the image memory is configured to store a plurality of three dimensional images and a plurality of front images received by the second communication circuit,
the second processor is configured to perform at least one of machine learning and data mining, based on the plurality of three dimensional images and the plurality of front images,
the knowledge memory is configured to store knowledge, based on the plurality of three dimensional images and the plurality of front images, acquired by the second processor, and
the third processor is configured to generate diagnosis support information by performing inference based on a three dimensional image and a front image of a subject's eye transmitted from one of the plurality of slit lamp microscopes and received by the second communication circuit and based on the knowledge stored in the knowledge memory.

11. The ophthalmic system of claim 2, wherein
the image acquisition unit is configured to further acquire a front image by photographing the subject's eye,
the first communication circuit is configured to transmit the front image together with the three dimensional image,
the second communication circuit is configured to receive the three dimensional image and the front image transmitted by the first communication circuit,
the image memory is configured to store a plurality of three dimensional images and a plurality of front images received by the second communication circuit,
the second processor is configured to perform at least one of machine learning and data mining, based on the plurality of three dimensional images and the plurality of front images,
the knowledge memory is configured to store knowledge, based on the plurality of three dimensional images and the plurality of front images, acquired by the second processor, and
the third processor is configured to generate diagnosis support information by performing inference based on a three dimensional image and a front image of a subject's eye transmitted from one of the plurality of slit lamp microscopes and received by the second communication circuit and based on the knowledge stored in the knowledge memory.

12. The ophthalmic system of claim 3, wherein
the image acquisition unit is configured to further acquire a front image by photographing the subject's eye,
the first communication circuit is configured to transmit the front image together with the three dimensional image,
the second communication circuit is configured to receive the three dimensional image and the front image transmitted by the first communication circuit,
the image memory is configured to store a plurality of three dimensional images and a plurality of front images received by the second communication circuit,
the second processor is configured to perform at least one of machine learning and data mining, based on the plurality of three dimensional images and the plurality of front images,
the knowledge memory is configured to store knowledge, based on the plurality of three dimensional images and the plurality of front images, acquired by the second processor, and
the third processor is configured to generate diagnosis support information by performing inference based on a three dimensional image and a front image of a subject's eye transmitted from one of the plurality of slit lamp microscopes and received by the second communication circuit and based on the knowledge stored in the knowledge memory.

13. The ophthalmic system of claim 1, wherein
each of the plurality of ophthalmic imaging apparatuses further includes a receiving circuit configured to receive subject information,
the first communication circuit is configured to transmit the subject information together with the three dimensional image,
the second communication circuit is configured to receive the three dimensional image and the subject information transmitted by the first communication circuit,
the image memory is configured to store a plurality of three dimensional images and a plurality of pieces of subject information received by the second communication circuit,
the second processor is configured to perform at least one of machine learning and data mining, based on the plurality of three dimensional images and the plurality of pieces of subject information,
the knowledge memory is configured to store knowledge, based on the plurality of three dimensional images and the plurality of pieces of subject information, acquired by the second processor, and
the third processor is configured to generate diagnosis support information by performing inference based on a three dimensional image of the subject's eye and subject information transmitted from one of the plurality of slit lamp microscopes and received by the second communication circuit and based on the knowledge stored in the knowledge memory.

14. The ophthalmic system of claim 2, wherein
each of the plurality of ophthalmic imaging apparatuses further includes a receiving circuit configured to receive subject information,
the first communication circuit is configured to transmit the subject information together with the three dimensional image,
the second communication circuit is configured to receive the three dimensional image and the subject information transmitted by the first communication circuit,
the image memory is configured to store a plurality of three dimensional images and a plurality of pieces of subject information received by the second communication circuit,
the second processor is configured to perform at least one of machine learning and data mining, based on the plurality of three dimensional images and the plurality of pieces of subject information,
the knowledge memory is configured to store knowledge, based on the plurality of three dimensional images and the plurality of pieces of subject information, acquired by the second processor, and the third processor is configured to generate diagnosis support information by performing inference based on a three dimensional image of the subject's eye and subject information transmitted from one of the plurality of slit lamp microscopes and received by the second communication circuit and based on the knowledge stored in the knowledge memory.

15. The ophthalmic system of claim 3, wherein
each of the plurality of ophthalmic imaging apparatuses further includes a receiving circuit configured to receive subject information,
the first communication circuit is configured to transmit the subject information together with the three dimensional image,
the second communication circuit is configured to receive the three dimensional image and the subject information transmitted by the first communication circuit,
the image memory is configured to store a plurality of three dimensional images and a plurality of pieces of subject information received by the second communication circuit,
the second processor is configured to perform at least one of machine learning and data mining, based on the plurality of three dimensional images and the plurality of pieces of subject information,
the knowledge memory is configured to store knowledge, based on the plurality of three dimensional images and the plurality of pieces of subject information, acquired by the second processor, and
the third processor is configured to generate diagnosis support information by performing inference based on a three dimensional image of the subject's eye and subject information transmitted from one of the plurality of slit lamp microscopes and received by the second communication circuit and based on the knowledge stored in the knowledge memory.

16. An ophthalmic information processing device comprising:
a communication circuit configured to receive three dimensional images of subject's eyes acquired by a plurality of ophthalmic imaging apparatuses via a communication path, the plurality of ophthalmic imaging apparatuses including a plurality of slit lamp microscopes;
an image memory configured to store a plurality of three dimensional images received by the communication circuit;
a first processor configured to perform at least one of machine learning and data mining, based on the plurality of three dimensional images;
a knowledge memory configured to store knowledge acquired by the first processor; and
a second processor configured to generate diagnosis support information by performing inference based on a three dimensional image of a subject's eye transmitted from one of the plurality of slit lamp microscopes and received by the communication circuit and based on the knowledge stored in the knowledge memory, wherein
each of the plurality of slit lamp microscopes includes
a third processor,
an illumination system configured to project slit light onto the subject's eye from a first direction,
a photographing system having a sensor configured to perform photography of the subject's eye in a second direction different from the first direction to acquire the three dimensional images, and
a movement mechanism configured to move the illumination system and the photographing system under control of the third processor.

17. An ophthalmic information processing device comprising:
a knowledge memory configured to store knowledge acquired by performing at least one of machine learning and data mining based on a plurality of three dimensional images acquired by a plurality of ophthalmic imaging apparatuses including a plurality of slit lamp microscopes;
a communication circuit configured to receive a three dimensional image of a subject's eye acquired by a slit lamp microscope via a communication path; and
a first processor configured to generate diagnosis support information by performing inference based on the three dimensional image and the knowledge stored in the knowledge memory, wherein
each of the plurality of slit lamp microscopes includes
a second processor,
an illumination system configured to project slit light onto the subject's eye from a first direction,
a photographing system having a sensor configured to perform photography of the subject's eye in a second direction different from the first direction to acquire the three dimensional images, and
a movement mechanism configured to move the illumination system and the photographing system under control of the second processor.

18. An ophthalmic diagnosing method comprising:
photographing subject's eyes and acquiring a plurality of three dimensional images by a plurality of ophthalmic imaging apparatuses including a plurality of slit lamp microscopes;
transmitting, by a first communication circuit in each of the slit lamp microscopes, the plurality of three dimensional images to an information processing system via a communication path;
receiving the plurality of three dimensional images by the information processing system:
storing the plurality of three dimensional images by the information processing system;
acquiring knowledge by performing at least one of machine learning and data mining based on the plurality of three dimensional images by the information processing system;
storing the knowledge by the information processing system; and
generating diagnosis support information by performing inference based on a three dimensional image of a subject's eye transmitted from a slit lamp microscope and the knowledge stored in the knowledge memory, wherein
each of the plurality of slit lamp microscopes includes
a processor,
an illumination system configured to project slit light onto the subject's eye from a first direction,
a photographing system having a sensor configured to perform photography of the subject's eye in a second direction different from the first direction to acquire a three dimensional image,
a movement mechanism configured to move the illumination system and the photographing system under control of the processor, and
the first communication circuit.

* * * * *